US012049438B2

United States Patent
Grasso et al.

(10) Patent No.: US 12,049,438 B2
(45) Date of Patent: Jul. 30, 2024

(54) PROCESS FOR METHANOL SYNTHESIS FROM CO2-RICH SYNGAS

(71) Applicant: TOTALENERGIES ONETECH, Courbevoie (FR)

(72) Inventors: Giacomo Grasso, Genval (BE); Daniel Curulla-Ferre, Uccle (BE); Joseph Stewart, Uccle (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/037,312

(22) PCT Filed: Nov. 12, 2021

(86) PCT No.: PCT/EP2021/081524
§ 371 (c)(1),
(2) Date: May 16, 2023

(87) PCT Pub. No.: WO2022/106313
PCT Pub. Date: May 27, 2022

(65) Prior Publication Data
US 2023/0391698 A1 Dec. 7, 2023

(30) Foreign Application Priority Data
Nov. 17, 2020 (EP) .................................... 20315455

(51) Int. Cl.
*C07C 29/153* (2006.01)
*B01J 21/06* (2006.01)
(Continued)

(52) U.S. Cl.
CPC .......... *C07C 29/153* (2013.01); *B01J 21/066* (2013.01); *B01J 23/62* (2013.01); *B01J 23/80* (2013.01);
(Continued)

(58) Field of Classification Search
CPC ... C07C 29/152; C07C 29/153; C07C 29/154; C07C 31/04; B01J 21/066; B01J 23/62; B01J 23/80
See application file for complete search history.

(56) References Cited

U.S. PATENT DOCUMENTS 5,631,302 A * 5/1997 Konig .................... B01J 8/0488
518/706
2011/0065966 A1 3/2011 Mueller et al.
(Continued)

FOREIGN PATENT DOCUMENTS

WO 2017019961 A1 2/2017

OTHER PUBLICATIONS

Search Report dated Jan. 13, 2022 issued in corresponding International Application No. PCT/EP2021/081524.
(Continued)

*Primary Examiner* — Jafar F Parsa
(74) *Attorney, Agent, or Firm* — Nath, Goldberg & Meyer; Joshua B. Goldberg

(57) ABSTRACT

The disclosure describes a process for methanol synthesis remarkable in that it comprises the steps of (a) providing syngas (3), (b) providing at least one first catalytic composition (9) comprising at least one first methanol synthesis catalyst; (c) putting into contact said syngas (3) with said first catalytic composition (9) under first temperature conditions, to provide a first gaseous effluent (15); (d) providing at least one second catalytic composition (17) comprising at least one second methanol synthesis catalyst; (e) putting into contact at least a part of said first gaseous effluent (15) with said second catalytic composition (17), to provide a second gaseous effluent (23) and a second liquid effluent (21); (f) recovering methanol from first (15) and/or second (23) gaseous effluent. The use of a first catalytic composition (9)
(Continued)

that comprises at least one first methanol synthesis catalyst in such a process for methanol synthesis is also described.

20 Claims, 6 Drawing Sheets

(51) Int. Cl.
*B01J 23/62* (2006.01)
*B01J 23/80* (2006.01)
*B01J 37/02* (2006.01)
*B01J 37/03* (2006.01)
*C07C 29/152* (2006.01)
*C07C 29/154* (2006.01)

(52) U.S. Cl.
CPC ......... *B01J 37/0201* (2013.01); *B01J 37/035* (2013.01); *B01J 37/038* (2013.01); *C07C 29/152* (2013.01); *C07C 29/154* (2013.01)

(56) References Cited

U.S. PATENT DOCUMENTS

2011/0178188 A1 7/2011 Kopetsch et al.
2021/0322957 A1* 10/2021 Stewart ................ B01J 35/0013

OTHER PUBLICATIONS

International Preliminary Report on Patentability dated Mar. 27, 2023 issued in corresponding International Application No. PCT/EP2021/081524.
International Preliminary Report on Patentability Annex dated Sep. 2, 2022 issued in corresponding International Application No. PCT/EP2021/081524.

* cited by examiner

PROCESS FOR METHANOL SYNTHESIS FROM CO2-RICH SYNGAS

This is a National Phase Application filed under 35 U.S.C. 371 as a national stage of PCT/EP2021/081524, filed Nov. 12, 2021, an application claiming the benefit of European Application No. 20315455.4, filed Nov. 17, 2020, the content of each of which is hereby incorporated by reference in its entirety.

FIELD OF THE DISCLOSURE

The present disclosure relates to a process for methanol synthesis from syngas.

TECHNICAL BACKGROUND

Methanol is widely used in different applications such as the synthesis of formaldehyde, which is then involved in the manufacture of plastic materials, paints, and textiles, for instance; the production of dimethyl ether, which may be used in aerosols or as an alternative fuel for diesel engines; the transesterification of triglycerides to produce biodiesel; or as a solvent or a fuel for engines.

Methanol is commercially produced from synthesis gas (syngas), i.e., a mixture of carbon oxides (i.e., carbon monoxide (CO) and/or carbon dioxide ($CO_2$)) and hydrogen ($H_2$) that can be produced from a variety of carbonated sources. CO and $CO_2$ react with $H_2$ according to the following equations:

$$CO + 2H_2 \rightleftharpoons CH_3OH \quad (1)$$

$$CO_2 + 3H_2 \rightleftharpoons CH_3OH + H_2O \quad (2)$$

$$CO + H_2O \rightleftharpoons CO_2 + H_2 \quad (3)$$

wherein the third one corresponds to the water-gas shift (WGS) reaction.

A widely used catalyst is $Cu/ZnO/Al_2O_3$ (CuZnAl), described for instance in GB1159035.

Usually, a syngas feed stream containing about 3 vol % $CO_2$ is used in the methanol synthesis process. This amount of 3 vol % is an optimal value since it has been demonstrated that increasing the content of $CO_2$ in the syngas feed is detrimental (Sahibzada, M. et al: *J. Catal,* 1998, 174, 111-118; Martin, O. and Pérez-Ramírez, J.; *Catal. Sci. Technol.* 2013, 3, 3343-3352) to methanol productivity due to the large amount of co-produced water, which strongly inhibits the catalyst activity and results in the loss of catalyst stability. Water is produced directly in the hydrogenation of $CO_2$ to methanol, and also in the reverse water-gas shift (RWGS) reaction which competes with the hydrogenation reaction.

The use of larger amounts of $CO_2$ in the production of methanol is of interest because $CO_2$ is a green-house gas intimately related to industrial activity and modern society and therefore such use could help in reducing the $CO_2$ footprint of industries.

Most of the current research in methanol synthesis from $CO_2$ has been focusing on the optimization of the commercially-available Cu/Zn/Al catalyst to prevent its deactivation in the presence of water or to inhibit the RWGS reaction, as described for example in "Zinc-rich copper catalysts promoted by gold for methanol synthesis" by Martin, O. et al.; *ACS Catal.* 2015, 5, 5607-5616.

Despite the improvements, these issues have not been overcome entirely. Thus, novel catalyst formulations have been investigated, such as $Cu-ZnO-Ga_2O_3/SiO_2$ in Toyir, J. et al.; *Appl. Catal., B* 2001, 29, 207-215; or Pd—ZnO/CNT in Liang, X. L. et al.; *Appl. Catal.,* B2009, 88, 315-322; or Cu/TaC in Dubois, J. L. et al.; *Chem. Lett.* 1992, 21, 5-8; or $LaCr_{0.5}Cu_{0.5}O_3$ in Jia, L. et al.; *Catal. Commun.* 2009, 10, 2000-2003.

Of these, only $Cu-ZnO-Ga_2O_3/SiO_2$ displayed both high activity and selectivity (99.5%). However, also optimized catalysts with low Cu content have been shown to suffer from $H_2O$ inhibition, limiting their exploitation only at low conversion levels (Martin et al.; *ACS Catal.* 2015, 5, 5607-5616). Moreover, little or no data exist to evaluate the long-term stability of such catalysts in the $CO_2$ hydrogenation reaction to methanol.

Indium oxide ($In_2O_3$) has recently been identified as a potential good catalyst for $C_{O2}$ hydrogenation into methanol based on density-functional-theory calculations in "*Active Oxygen Vacancy Site for Methanol Synthesis from $CO_2$ Hydrogenation on $In_2O_3(110)$: a DFT study*" Ye, J. et al.; *ACS Catal.* 2013, 3, 1296-1306. This study indicates that the oxygen-defective $In_2O_3(110)$ surface can activate $CO_2$ and hydrogenate it via HCOO and $H_3CO$ species to methanol. An experimental study over commercially available $In_2O_3$ demonstrated reasonable $CO_2$ conversion for this catalyst but only low selectivity in "Hydrogenation of $CO_2$ to methanol over $In_2O_3$ catalyst" Sun, K. et al., J. $CO_2$ Util. 2015, 12, 1-6.

In EP 3 034 161, a reactor has been designed with two reactors for the production of methanol. The liquid stream that is produced after contacting the syngas feedstream with the first reactor is removed from the reactor design using a solvent, typically alcohol, capable of absorbing the methanol and the water. The removal of the products from the first reactor is an application from the Le Chatelier's principle and is enhancing the conversion of the reactant by properly managing the thermodynamics of the reactions (1), (2) and (3). However, it does not address the problem of using a $CO_2$-rich syngas feedstream.

US2011/0178188 and US2011065966 are about process for producing methanol from a synthesis gas containing hydrogen and carbon oxides wherein the synthesis gas is passed through a first, water-cooled, reactor in which a part of the carbon oxides is catalytically converted to methanol. The resulting mixture containing synthesis gas and methanol vapor is supplied to a second, gas-cooled, reactor in which a further part of the carbon oxides is converted to methanol. Subsequently, methanol is separated from the synthesis gas, and synthesis gas is recirculated to the first reactor. The cooling gas flows through the second reactor co-current to the mixture withdrawn from the first reactor. These documents are silent about the use of $CO_2$-rich syngas feed stream and how to reduce deactivation of the catalyst due to the presence of a high content of $CO_2$ in the syngas.

WO2014206635 is about a process for the preparation of methanol in parallel reactors, comprising the steps of (a) reacting carbon oxides and hydrogen in the presence of a methanol catalyst in a first methanol reactor to obtain a first methanol-containing effluent, (b) introducing and reacting unconverted synthesis gas in a second methanol reactor in the presence of a methanol catalyst to obtain a second methanol-containing effluent, the first methanol reactor and the second methanol reactor being connected in parallel, (c) combining the first and second effluent, and (d) cooling and separating the combined and cooled effluent into a methanol-containing liquid phase and unconverted synthesis gas, the methanol catalyst in the first methanol reactor is indirectly cooled by boiling water and the methanol catalyst in the second methanol reactor is either directly or indirectly cooled by the unconverted synthesis gas prior to conversion into the second effluent. Here again the use of $CO_2$-rich syngas feed stream is not treated.

There is still a need for a process of methanol synthesis which can convert a $CO_2$-rich syngas feed stream into methanol without being subject to deactivation of the catalyst.

SUMMARY OF THE DISCLOSURE

According to a first aspect, the disclosure provides a process for methanol synthesis remarkable in that it comprises the following steps:
  a. providing a syngas feedstream comprising hydrogen and carbon oxides, wherein the carbon oxides are selected from carbon dioxide or a mixture of carbon dioxide and carbon monoxide provided that the molar ratio of carbon dioxide over carbon monoxide ($CO_2$/CO) in the mixture is equal to or greater than 1.0, and that said syngas feedstream comprises at least 12.0 mol % of $CO_2$ based on the total molar content of said syngas feedstream;
  b. providing a first catalytic composition that comprises at least one first methanol synthesis catalyst;
  c. putting into contact said syngas feedstream with said first catalytic composition under first reaction conditions comprising first temperature conditions, to provide a first gaseous effluent and optionally a first liquid effluent;
  d. providing a second catalytic composition that comprises at least one second methanol synthesis catalyst wherein said at least one second methanol synthesis catalyst is the same or different from said one first methanol synthesis catalyst;
  e. putting into contact at least a part of said first gaseous effluent with the second catalytic composition under second reaction conditions comprising second temperature conditions, to provide a second gaseous effluent and a second liquid effluent;
  f. recovering methanol from one or more selected from the first gaseous effluent and the second gaseous effluent, wherein the first temperature conditions are at least 270° C. and wherein the second temperature conditions are lower than the first temperature conditions and second temperature conditions are ranging between 180° C. and 250° C.

With preference, the first temperature conditions comprise a temperature ranging between 270° C. and 350° C., more preferably between 280° C. and 340° C., even more preferably between 290° C. and 340° C.

Also, one or more of the following features can be advantageously used to further define the first temperature conditions under which the process can occur according to the disclosure:
  Said first temperature conditions are at least 275° C., preferably at least 280° C., more preferably at least 285° C., even more preferably at least 290° C., most preferably at least 280° C., even most preferably at least 290° C., or at least 300° C.
  Said first temperature conditions are at most 350° C., more preferably at most 340° C.
  The first temperature conditions are the start-of-run temperature conditions.

It has been found that is possible to provide a process for methanol synthesis from syngas in which the catalyst for doing the conversion of syngas to methanol can be protected from the $CO_2$ comprised in a $CO_2$-rich syngas. Using a sequence of two catalytic compositions placed in two subsequent reactors allows working under different reaction conditions to convert the syngas into methanol. To produce methanol within the first reactor allows decreasing the amount of carbon dioxide into the first gaseous effluent produced after contact with the first catalytic composition. The second catalytic composition (which can be the same than the first catalytic composition or different) is placed downstream of the first catalytic composition and is therefore contacted with a feedstream having a reduced amount of $CO_2$, which allows the second catalytic composition to be worked under softer conditions and subsequently to be kept running for a longer period. The lower $CO_2$/CO molar ratio in the first gaseous effluent compared to the higher $CO_2$/CO molar ratio in the syngas feedstream allows to not deactivate or to deactivate to a lesser degree the second catalytic composition. The disclosed process has further allowed improving the rate of conversion of syngas to methanol, wherein the syngas is $CO_2$-rich.

With preference, the second temperature conditions are the same or lower than the first temperature conditions. More preferably, the second temperature conditions are lower than the first temperature conditions. This allows the second catalytic composition to perform more optimally.

As after step (c), methanol is produced, the first catalytic composition is therefore different from a guard bed since a guard bed would perform reverse water-gas shift reaction resulting in the production of CO as the main product. Advantageously, the content of methanol that can be found in the first gaseous effluent is ranging from 1.0 to 21.0 mol % based on the total molar content of the first gaseous effluent. With preference, the first gaseous effluent comprises at least 1.0 mol % of methanol based on the total molar content of the first gaseous effluent, more preferably at least 2.0 mol %. The first effluent exiting the reactor is gaseous. The first gaseous effluent is optionally separated into a first liquid effluent and a first dried gaseous effluent.

With preference, one or more of the following features can be used to better define the syngas feedstream:
  When the carbon oxides present in the syngas feedstream is a mixture of carbon dioxide and carbon monoxide, said mixture has a molar ratio of carbon dioxide over carbon monoxide ($CO_2$/CO) equal to or greater than 1.5, preferably equal to or greater than 2.0, or equal to or greater than 2.5; more preferably equal to or greater than 3.0 or equal to or greater than 3.5, even more preferably equal to or greater than 4.0 or equal to or greater than 5.0, most preferably equal to or greater than 8.0, and even most preferably equal to or greater than 10.0.
  The syngas feedstream comprises hydrogen and carbon oxides (i.e. $H_2/(CO+CO_2)$ ratio) in a molar ratio hydrogen over carbon oxides ranging between 2 and 5; preferably between 3 and 4.
  The molar ratio of hydrogen to carbon dioxide ($H_2/CO_2$) in the syngas feedstream is at least 2.0, preferably it is at least 2.5 or at least 2.8, more preferably it is at least 3.0.
  The molar ratio of hydrogen to carbon dioxide ($H_2/CO_2$) in the syngas feedstream is at most 10.0, preferably it is at most 7.5 or at most 5.0, more preferably it is at most 4.5.
  The syngas feedstream comprises more than 12.0 mol % of $CO_2$ based on the total molar content of the syngas feedstream, preferably at least 15.0 mol %, more preferably at least 18.0 mol % and even more preferably at least 20.0 mol %, or at least 22.0 mol %.

The syngas feedstream comprises inert gas at a concentration which is inferior to 0.5 vol. % based on the total volume of said syngas feedstream, preferably inferior to 0.4 vol. %, or inferior to 0.3 vol. %, or inferior to 0.2 vol. %, or inferior to 0.1 vol. %. For example, inert gas for the said reaction is or comprises nitrogen, helium and/or argon.

The syngas feedstream comprises methane at a concentration which is inferior to 0.5 vol. % based on the total volume of said syngas feedstream, preferably inferior to 0.4 vol. %, or inferior to 0.3 vol. %, or inferior to 0.2 vol. %, or inferior to 0.1 vol. %.

For example, the first catalytic composition is the same or different from the second catalytic composition; preferably, the first catalytic composition and the second catalytic composition are the same.

In a preferred embodiment, at least one first methanol synthesis catalyst and at least one second methanol synthesis catalyst are the same.

Advantageously, the methanol synthesis catalyst is or comprises a copper zinc oxide catalyst. In an alternative embodiment, at least one first methanol synthesis catalyst and at least one second methanol synthesis catalyst are different. With preference, the at least one first methanol synthesis catalyst is or comprises a copper zinc oxide catalyst and/or at least one second methanol synthesis catalyst is a methanol synthesis catalyst which is different from a copper zinc oxide catalyst.

Whichever embodiment is chosen, at least one first methanol synthesis catalyst and/or at least one second methanol synthesis catalyst is or comprises a copper zinc oxide catalyst or an indium oxide catalyst. It is advantageous that the copper zinc oxide catalyst is prepared by co-precipitation and/or that the indium oxide catalyst comprises a promoter comprising at least one metal, preferably at least one metal selected from ruthenium, rhodium, gold, iridium, palladium, silver, osmium, platinum, copper, nickel, cobalt and any combination thereof, more preferably palladium.

Whichever embodiment is chosen, at least one first methanol synthesis catalyst and/or at least one second methanol synthesis catalyst is or comprises one or more selected from a copper zinc oxide catalyst, an indium oxide catalyst, ZnO, Au/ZnO, Au/Fe$_2$O$_3$, Au/TiO$_2$, Au/ZrO$_2$, Au/La$_2$O$_3$, Au/ZnFe$_2$O$_4$, Fe$_2$O$_3$, Au/Fe$_2$O$_3$, CeO$_2$, TiO$_2$, ZrO$_2$, La$_2$O$_3$, Zn/Fe$_2$O$_3$; preferably selected from an indium oxide catalyst, Cu—ZnO, Cu—ZnO/Al$_2$O$_3$, Cu—ZnO—Ga$_2$O$_3$/SiO$_2$, Cu—ZnO—Al$_2$O$_3$/ZrO$_2$, ZnO, Au/ZnO, Au/Fe$_2$O$_3$, Au/TiO$_2$, Au/ZrO$_2$, Au/La$_2$O$_3$, Au/ZnFe$_2$O$_4$, Fe$_2$O$_3$, Au/Fe$_2$O$_3$, Cu/ZnO, CeO$_2$, TiO$_2$, ZrO$_2$, La$_2$O$_3$, Zn/Fe$_2$O$_3$; more preferably Cu—ZnO/Al$_2$O$_3$, Cu—ZnO—Ga$_2$O$_3$/SiO$_2$, and Cu—ZnO—Al$_2$O$_3$/ZrO$_2$; even more preferably from Cu—ZnO—Al$_2$O$_3$/ZrO$_2$.

With preference, one or more of the following features define the first catalytic composition that comprises at least one first methanol synthesis catalyst and which is provided in step (b) of the process for methanol synthesis according to the disclosure:
  Said first catalytic composition is activated respectively before step (c).
  Said first catalytic composition comprises one or more first methanol synthesis catalysts with a surface area in the range of 5 m$^2$g$^{-1}$ to 400 m$^2$g$^{-1}$, as determined by N$_2$ sorption analysis according to ASTM D3663-03.

With preference, one or more of the following features define the second catalytic composition that comprises at least one second methanol synthesis catalyst and which is provided in step (d) of the process for methanol synthesis according to the disclosure:
  Said second catalytic composition is activated respectively before step (e).
  Said second catalytic composition comprises one or more second methanol synthesis catalysts with a surface area in the range of 5 m$^2$g$^{-1}$ to 400 m$^2$g$^{-1}$, as determined by N$_2$ sorption analysis according to ASTM D3663-03.

Advantageously, when the at least one first methanol synthesis catalyst and/or the at least one second methanol synthesis catalyst is or comprises a copper zinc oxide catalyst, one or more of the following features define said copper zinc oxide catalyst:
  Said copper zinc oxide catalyst is selected from Cu/ZnO, Cu—ZnO/Al$_2$O$_3$, Cu—ZnO—Ga$_2$O$_3$/SiO$_2$, Cu—ZnO—Al$_2$O$_3$/ZrO$_2$ and any mixture thereof; preferably said copper zinc oxide catalyst is or comprises Cu—ZnO—Al$_2$O$_3$/ZrO$_2$.
  Said copper zinc oxide catalyst is activated before step (c) and/or step (e); preferably by reduction with hydrogen.
  Said copper zinc oxide catalyst is prepared by co-precipitation.
  Said copper zinc oxide catalyst is a activated supported catalyst and/or has a surface area in the range of about 5 m$^2$ g$^{-1}$ to about 400 m$^2$ g$^{-1}$, such as from 30 m$^2$ g$^{-1}$ to about 200 m$^2$ g$^{-1}$ as determined according to N$_2$ sorption analysis according to ASTM D3663-03.

Advantageously, when the at least one first methanol synthesis catalyst and/or the at least one second methanol synthesis catalyst is or comprises an indium oxide catalyst, one or more of the following features define said indium oxide catalyst:
  Said indium oxide catalyst comprises indium oxide in the form of In$_2$O$_3$.
  Said indium oxide catalyst further comprises a promoter comprising at least one metal. With preference, said at least one metal is selected from ruthenium (Ru), rhodium (Rh), gold (Au), iridium (Ir), palladium (Pd), silver (Ag), osmium (Os), platinum (Pt), copper (Cu), nickel (Ni), cobalt (Co) and any combinations thereof; preferably said at least one metal is selected from nickel (Ni), palladium (Pd), platinum (Pt) and any combination thereof; more preferably, said at least one metal is selected from palladium (Pd) and/or platinum (Pt); even more preferably, said at least one metal is palladium (Pd). For example, the indium oxide catalyst further comprises a promoter comprising or being palladium (Pd). For example, the indium oxide catalyst further comprises a promoter comprising or being platinum (Pt). For example, the indium oxide catalyst further comprises a promoter comprising or being nickel (Ni).
  Said indium oxide catalyst is activated before step (c) and/or step (e); preferably by thermal activation.
  The indium oxide catalyst is a activated supported catalyst and/or has a surface area in the range of about 5 m$^2$ g$^{-1}$ to about 400 m$^2$ g$^{-1}$, such as from 30 m$^2$ g$^{-1}$ to about 200 m$^2$ g$^{-1}$ as determined according to N$_2$ sorption analysis according to ASTM D3663-03.
  The indium oxide catalyst is prepared by impregnation or by deposition precipitation or by co-precipitation, preferably by impregnation. For example, the indium oxide catalyst is prepared by wet impregnation.

Also, one or more of the following features can be advantageously used to further define the second temperature conditions under which the process can occur according to the disclosure:
- Said second temperature conditions are ranging between 180° C. and below 250° C.; preferably, between 190° C. and 245° C., more preferably between 200° C. and 240° C., even more preferably between 200° C. and 235° C.
- Said second temperature conditions are at least 180° C., preferably at least 190° C., more preferably at least 200° C.
- Said second temperature conditions are at most 250° C., preferably below 250° C., more preferably at most 245° C., even more preferably at most 240° C., and most preferably at most 235° C.
- The second temperature conditions are the start-of-run temperature conditions.

Also, one or more of the following features can be advantageously used to further define the reaction conditions under which the process can occur according to the disclosure:
- Said first reaction conditions further comprise first pressure conditions ranging between 0.5 and 12.0 MPa, preferably between 1.0 and 9.0 MPa, more preferably between 1.5 and 8.0 MPa.
- Said second reaction conditions further comprise second pressure conditions ranging between 0.5 and 12.0 MPa, preferably between 1.0 and 9.0 MPa, more preferably between 1.5 and 8.0 MPa.
- Said first and second reaction conditions further comprise respectively first and second pressure conditions which are similar.
- Said first reaction conditions further comprise a gas hourly space velocity of said syngas feedstream ranging between 1,000 and 100,000 $h^{-1}$, preferably between 5,000 and 50,000 $h^{-1}$.
- Said second reaction conditions further comprise a gas hourly space velocity of said first gaseous effluent ranging between 1,000 and 100,000 $h^{-1}$, preferably between 5,000 and 50,000 $h^{-1}$.
- Said first and second reaction conditions further comprise respectively a gas hourly space velocity of said syngas feedstream and a gas hourly space velocity of said first gaseous effluent which are identical.

With preference, one or more of the following features can be advantageously used to further define the process for methanol synthesis according to the disclosure:
- Said first gaseous effluent is subjected to a separation step before being put into contact with said second catalytic composition in step (e) to remove at least a part of methanol and water; with preference, said separation step is carried out by distillation.
- At least a part of the second gaseous effluent is recycled to be put into contact with said first catalytic composition again.
- Said first gaseous effluent is subjected to a separation step before being put into contact with said second catalytic composition in step (e) to remove at least a part of methanol and water; with preference, said separation step is carried out by distillation; and at least a part of the second gaseous effluent is recycled to be put into contact with said first catalytic composition again.
- At least a part of the first gaseous effluent is recycled to be put into contact with the first catalytic composition again.
- At least a part of the second gaseous effluent is recycled to be put into contact with the second catalytic composition again.
- At least a part of the first gaseous effluent is recycled to be put into contact with the first catalytic composition again and at least a part of the second gaseous effluent is recycled to be put into contact with the second catalytic composition again.

According to a second aspect, the disclosure provides a use of at least one first catalytic composition that comprises at least one first methanol synthesis catalyst in a process for methanol synthesis according to the first aspect, said use being remarkable in that it is performed in an installation comprising at least two reactors in series wherein
- a first reactor comprises said at least one first catalytic composition, and
- at least one subsequent reactor placed downstream of the first reactor comprises at least one second catalytic composition comprising at least one second methanol synthesis catalyst wherein at least one second methanol synthesis catalyst is the same or different from one first methanol synthesis catalyst;

wherein the use comprises providing a syngas feedstream comprising hydrogen and carbon oxides to the first reactor to contact said syngas feedstream with said at least first catalytic composition, wherein the carbon oxides are selected from carbon dioxide or a mixture of carbon dioxide and carbon monoxide provided that the molar ratio of carbon dioxide over carbon monoxide in the mixture is equal to or greater than 1.0; wherein said syngas feedstream comprises at least 12.0 mol % of $CO_2$ based on the total molar content of said syngas feedstream;

wherein the temperature within the first reactor is at least 270° C.; and further wherein the second temperature conditions are lower than the first temperature conditions and second temperature conditions are ranging between 180° C. and 250° C.

For example, the use is remarkable in that the installation further comprises a first gas/liquid separator disposed between the first reactor and at least one subsequent reactor. Advantageously, the use is remarkable in that the installation further comprises a splitter downstream of said first gas/liquid separator.

For example, the use is remarkable in that the installation further comprises a second gas/liquid separator disposed downstream of said at least one subsequent reactor. Advantageously, the use is remarkable in that the installation further comprises a splitter downstream of said second gas/liquid separator.

Advantageously, the at least one subsequent reactor comprising said at least one second catalytic composition forms at least one subsequent catalytic bed and at least one reverse water-gas shift catalyst is introduced in said one or more subsequent catalytic beds. With preference, at least one reverse water-gas shift catalyst is introduced at the end of said one or more subsequent catalytic beds. With preference, said one or more reverse water-gas shift catalysts are selected from $Fe_2O_3$, $ZnNiFe_2O_4$, $Ba$—$Fe_3O_3$—$Al_2O_3$—$NiO$, $Cu$—$Mn$ spinel oxide, $La_{2-x}Ca_xCuO_4$, oxide supported $Cu$, $CuO/ZrO_2$, $CeO_2/CuO$, oxide supported $Au$, $Cu$—$CeO_2$—$La_2O_3$.

For example, the first reactor comprising said at least one first catalytic composition forms a first catalytic bed and the temperature within said first reactor is the temperature at the exit of said first catalytic bed.

For example, the at least one subsequent reactor comprising said at least one second catalytic composition forms at least one subsequent catalytic bed and the temperature within said at least one subsequent reactor is the temperature at the exit of each of one or more subsequent catalytic beds.

DETAILED DESCRIPTION

Figure 1:
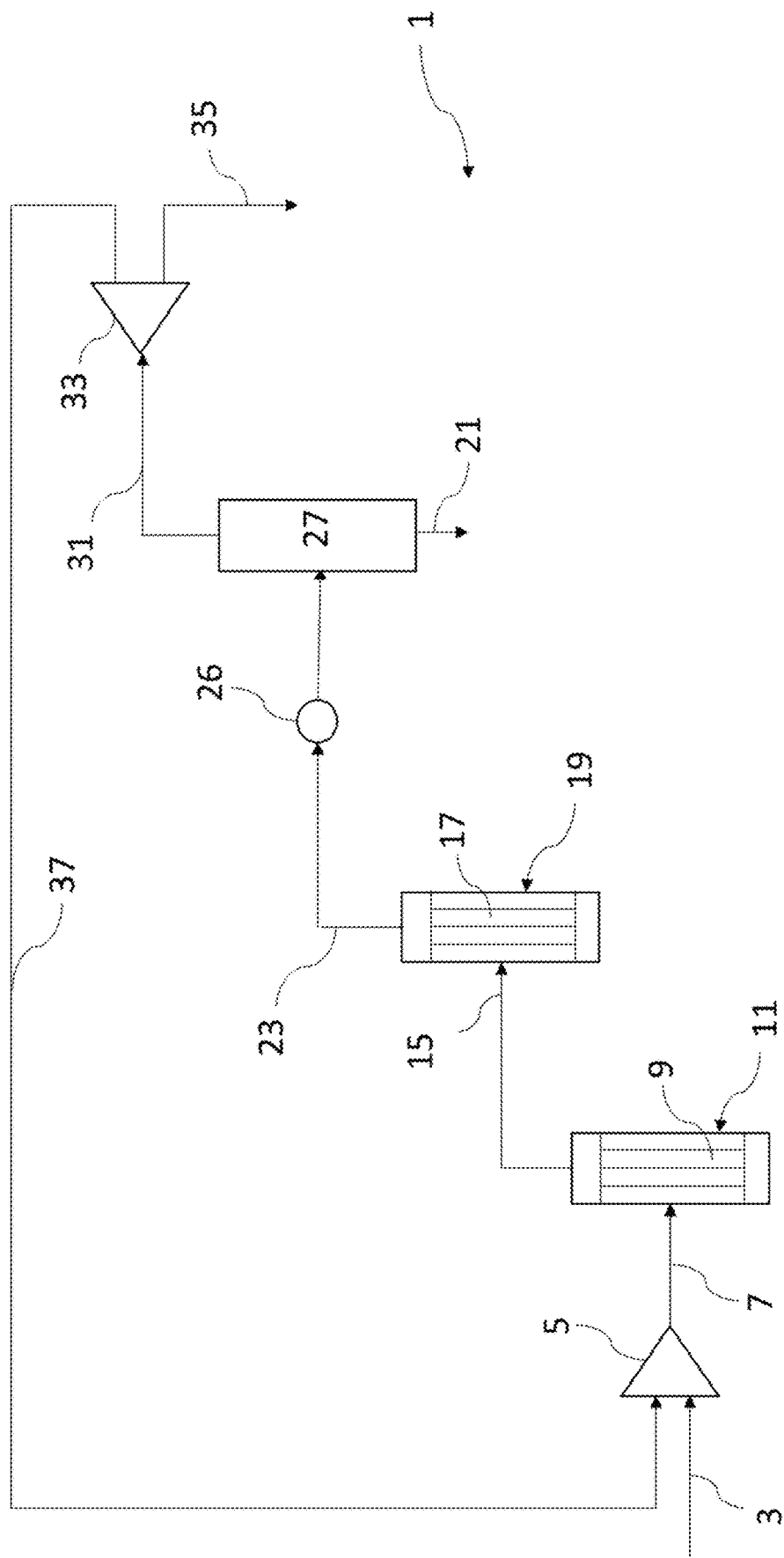
FIG. 1 illustrates a first embodiment of an installation to conduct the process according to the disclosure.

For the disclosure, the following definitions are given:

As used herein the generic term "catalyst" refers to both a "bulk" and a "supported catalyst". A bulk catalyst is a catalyst containing only the main active phase (i.e., indium oxide). A supported catalyst comprises the bulk catalyst and a support (e.g., $ZrO_2$). A metal promoted catalyst is a catalyst in which a metal has been added.

A co-precipitated catalyst is a catalyst wherein the active phase is intimately mixed with the support, in contrast with deposition precipitation techniques and impregnation techniques wherein the active phase is deposited on the support.

According to the disclosure, a supported catalyst comprises a catalyst and a support to provide mechanical support to the supported catalyst as well as to further enhance the exposure of a feedstream to active sites of the supported catalyst.

The metals that can be employed in the present disclosure are selected from Ru, Rh, Pd, Ag, Os, Pt, Cu, Ni, Co, Au and Ir. In a preferred embodiment of the disclosure, the catalyst is devoid of Au.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The yield of particular chemical compounds is determined as the mathematical product between the selectivity to said particular chemical compounds and the conversion rate of the chemical reaction. The mathematical product is expressed as a percentage.

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The Syngas Feedstream 3

In the methanol synthesis process according to the disclosure, a syngas feedstream 3 composed of hydrogen gas and carbon oxides (i.e. selected from carbon dioxide or a mixture of $CO_2$ and CO gases) is caused to interact subsequently with two catalytic compositions.

According to the disclosure, the syngas feedstream 3 is composed of hydrogen gas and carbon oxides, wherein the carbon oxides are selected from carbon dioxide or a mixture of carbon dioxide and carbon monoxide; with preference, the carbon oxides are a mixture of carbon dioxide and carbon monoxide.

When the syngas feedstream 3 comprises hydrogen and a mixture of carbon dioxide and carbon monoxide, the feedstream can be CO-rich or $CO_2$-rich. Per the disclosure, a $CO_2$-rich feedstream is employed. The $CO_2$-rich feedstream can have a molar ratio of carbon dioxide over carbon monoxide ($CO_2/CO$) that is equal to or greater than 1.0.

In a preferred embodiment, the syngas feedstream 3 comprises more than 12.0 mol % of $CO_2$ based on the total molar content of the syngas feedstream 3, preferably at least 15.0 mol %, more preferably at least 18.0 mol %, even more preferably at least 20.0 mol %, most preferably at least 22.0 mol %.

In a preferred embodiment, the syngas feedstream 3 comprises at most 40 mol % of $CO_2$ based on the total molar content of the syngas feedstream 3, preferably at most 35 mol %, more preferably at most 30 mol %; even more preferably at most 25 mol %.

In an embodiment, the syngas feedstream 3 comprises at most 10.0 mol % of carbon monoxide based on the total molar content of the syngas feedstream 3, preferably at most 5.0 mol %, more preferably at most 2.0 mol %, even more preferably at most 1.0 mol %, most preferably at most 0.5 mol %.

In an embodiment, the syngas feedstream 3 is devoid of carbon monoxide.

In a preferred embodiment, the syngas feedstream 3 comprises at most 90 mol % of $H_2$ based on the total molar content of the syngas feedstream 3, preferably at most 80 mol %, more preferably at most 70 mol %, even more preferably at most 60 mol %.

In a preferred embodiment, the syngas feedstream 3 comprises hydrogen and carbon oxides in a molar ratio hydrogen over carbon oxides (i.e. $H_2/(CO+CO_2)$ ratio) ranging between 2 and 5; preferably between 3 and 4.

In a preferred embodiment, wherein the syngas feedstream is a mixture of carbon dioxide and carbon monoxide; the molar ratio of carbon dioxide to carbon monoxide ($CO_2/CO$) in the syngas feedstream 3 (i.e. in the mixture) is equal to or greater than 1.5; preferably equal to or greater than 2.0, more preferably equal to or greater than 3.0, or equal to or greater than 3.5; even more preferably equal to or greater than 4.0 or equal to or greater than 5.0, most preferably equal to or greater than 8.0, and even most preferably equal to or greater than 10.0.

In a preferred embodiment, wherein the syngas feedstream is a mixture of carbon dioxide and carbon monoxide; the molar ratio of carbon dioxide to carbon monoxide ($CO_2/CO$) in the syngas feedstream 3 (i.e. in the mixture) is infinite (i.e. no carbon monoxide is present in the syngas feed stream 3), preferably at most 20.0, more preferably at most 15.0, even more preferably at most 10.0.

In an embodiment, wherein the syngas feedstream is a mixture of carbon dioxide and carbon monoxide; the molar ratio of carbon dioxide to carbon monoxide ($CO_2/CO$) in the syngas feedstream 3 (i.e., in the mixture) is ranging from 1.0 to 10.0, preferably ranging from 1.5 to 8.0; preferably ranging from 3.0 to 8.0.

In a preferred embodiment, the molar ratio of hydrogen to carbon dioxide ($H_2/CO_2$) in the syngas feedstream 3 is at least 2.0, preferably it is at least 2.5 or at least 2.8, more preferably it is at least 3.0 For example, the molar ratio of hydrogen to carbon dioxide ($H_2/CO_2$) in the syngas feedstream 3 is at most 10.0, preferably it is at most 7.5 or at most 5.0, more preferably it is at most 4.5.

The First Catalytic Composition 9

The process according to the disclosure comprises the use of a first catalytic composition 9 being susceptible to resist to a high concentration of carbon dioxide. Such first catalytic composition 9 comprises at least one first methanol synthesis catalyst. It is advantageous that said at least one first methanol synthesis catalyst is a copper zinc oxide catalyst or an indium oxide catalyst, preferably a copper zinc oxide catalyst.

With respect to indium oxide catalysts, upon standard reaction conditions, they are not deactivated when being in the presence of a high concentration of carbon dioxide. Similar behaviour is observed when copper zinc oxide catalysts have been used. Advantageously, indium oxide catalyst can further comprise a catalyst support. Indium oxide in the form of $In_2O_3$ deposited on a catalyst support and their method of preparation are known and described for example in WO2017/118572 and in WO2017/118573 which are incorporated by reference.

Therefore, the first temperature conditions that are provided upon reaction with the syngas feedstream 3 are ranging between 270° C. and 350° C., preferably between 275° C. and 345° C., more preferably between 280° C. and 340° C., even more preferably between 285° C. and 335° C. while the second temperature conditions are lower than the first temperature conditions and/or are ranging for example between 180° C. and 250° C., preferably between 180° C. and below 250° C.; more preferably, between 185° C. and 245° C., even more preferably between 190° C. and 250° C.; most preferably, between 190° C. and 240° C., even most preferably between 200° C. and 235° C.

For example, the first temperature conditions are at least 270° C., preferably at least 275° C., more preferably at least 280° C., even more preferably at least 285° C., most preferably at least 290° C., even most preferably at least 295° C., or at least 300° C. For example, the first temperature conditions are at most 350° C., preferably at most 345° C., more preferably at most 340° C.

For example, the second temperature conditions are at least 180° C., preferably at least 190° C., and more preferably at least 200° C. For example, the second temperature conditions are at most 250° C., preferably below 250° C.; more preferably at most 245° C. or at most 240° C., even more preferably at most 235° C.

The first temperature conditions are advantageously the start-of-run temperature conditions.

The first reaction conditions also comprise first pressure conditions ranging between 0.5 and 12.0 MPa, preferably between 1.0 and 9.0 MPa, more preferably between 1.5 and 8.0 MPa.

The first reaction conditions further comprise a gas hourly space velocity of said syngas feed stream 3 ranging between 1,000 and 100,000 $h^{-1}$, preferably between 2,500 and 75,000 $h^{-1}$, more preferably between 5,000 and 50,000 $h^{-1}$.

The at least one first methanol synthesis catalyst of the first catalytic composition 9 allows converting syngas into methanol and can be one or more selected from a copper zinc oxide catalyst and/or an indium oxide catalyst.

For example, at least one first methanol synthesis catalyst of the first catalytic composition 9 allows converting syngas into methanol and can be one or more selected from a copper zinc oxide catalyst an indium oxide catalyst $Al_2O_3/ZrO_2$, ZnO, Au/ZnO, $Au/Fe_2O_3$, $Au/TiO_2$, $Au/ZrO_2$, $Au/La_2O_3$, $Au/ZnFe_2O_4$, $Fe_2O_3$, $Au/Fe_2O_3$, $CeO_2$, $TiO_2$, $ZrO_2$, $La_2O_3$, $Zn/Fe_2O_3$.

For example, at least one first methanol synthesis catalyst of the first catalytic composition 9 allows converting syngas into methanol and can be one or more selected from an indium oxide catalyst Cu—ZnO/$Al_2O_3$, Cu—ZnO—$Ga_2O_3$/$SiO_2$, Cu—ZnO—$Al_2O_3$/$ZrO_2$, ZnO, Au/ZnO, $Au/Fe_2O_3$, $Au/TiO_2$, $Au/ZrO_2$, $Au/La_2O_3$, $Au/ZnFe_2O_4$, $Fe_2O_3$, $Au/Fe_2O_3$, Cu/ZnO, $CeO_2$, $TiO_2$, $ZrO_2$, $La_2O_3$, $Zn/Fe_2O_3$, preferably Cu—ZnO/$Al_2O_3$, Cu—ZnO—$Ga_2O_3$/$SiO_2$, and Cu—ZnO—$Al_2O_3$/$ZrO_2$; more preferably from Cu—ZnO—$Al_2O_3$/$ZrO_2$.

In the configuration of the present disclosure, at least one subsequent reactor 19 is placed downstream of said first reactor 11 and comprises one second catalytic composition 17 which comprises at least one second methanol synthesis catalyst. The presence of the first catalytic composition 9 comprising at least first methanol synthesis catalyst allows protecting the second methanol synthesis catalyst of the second catalytic composition 17 which is present downstream. This allows decreasing the content of the $CO_2$ in the first gaseous effluent 15 which is directed to the subsequent reactor or to the second reactor 19. This is why it is possible to undertake step (d) of the disclosed process at second temperature conditions lower than the first temperature conditions and subsequently improve the protection of the second catalytic composition 17 from deactivation.

The presence of the first catalytic composition 9 comprising at least one first methanol synthesis catalyst allows producing methanol already in the first reactor 11, increasing, therefore, the overall yield of the process. For example, the first gaseous effluent comprises at least 1.0 mol % of methanol based on the total molar content of the first gaseous effluent, more preferably at least 2.0 mol %, even more preferably at least 5.0 mol %, most preferably at least 10.0 mol. %, and the content of methanol that can be found in the first gaseous effluent can be ranging from 1.0 to 21.0 mol % based on the total molar content of the first gaseous effluent, preferably from 2.0 to 15.0 mol %.

The Second Catalytic Composition 17

According to the disclosure, a second catalytic composition 17 suitable for methanol synthesis is provided downstream of said first catalytic composition 9 comprising at least one first methanol synthesis catalyst, wherein said second catalytic composition 17 comprises at least one second methanol synthesis catalyst. The second catalytic composition 17 can be the same or different from the first catalytic composition 9. For example, at least one second methanol synthesis catalyst is the same or different from said one first methanol synthesis catalyst. Advantageously, the second catalytic composition 17 is the same the first catalytic composition 9. Alternatively, the second catalytic composition 17 is different from the first catalytic composition 9, i.e., the second catalytic composition 17 comprises one or more second methanol synthesis catalysts which are different than the one or more first methanol synthesis catalysts of the first catalytic composition 9.

The second catalytic composition 17 is present in one or more second reactors 19 placed downstream of the first reactor 11.

Nevertheless, when said at least one second methanol synthesis catalyst is an indium oxide catalyst, or preferably an copper zinc oxide catalyst, and is subsequently present in the second reactor 19, said catalyst is preferably placed in a first reaction zone of the second reactor 19, the other second methanol synthesis catalyst different from indium oxide catalyst, or different from copper zinc oxide catalyst respectively, being placed in a subsequent reaction zone being downstream of said first reaction zone. The idea behind such configuration is to reduce as much as possible the content of $CO_2$ in the gaseous effluent 15 before it contacts the second catalytic composition to avoid its deactivation and to enhance its stability.

With preference, the at least one second methanol synthesis catalyst is one or more selected from a copper zinc oxide catalyst, an indium oxide catalyst, ZnO, Au/ZnO, $Au/Fe_2O_3$, $Au/TiO_2$, $Au/ZrO_2$, $Au/La_2O_3$, $Au/ZnFe_2O_4$, $Fe_2O_3$, $Au/Fe_2O_3$, $CeO_2$, $TiO_2$, $ZrO_2$, $La_2O_3$, $Zn/Fe_2O_3$, and a combination thereof; preferably selected from an indium oxide catalyst, Cu—$ZnO/Al_2O_3$, Cu—ZnO—$Ga_2O_3/SiO_2$, Cu—ZnO—$Al_2O_3/ZrO_2$, ZnO, Au/ZnO, $Au/Fe_2O_3$, $Au/TiO_2$, $Au/ZrO_2$, $Au/La_2O_3$, $Au/ZnFe_2O_4$, $Fe_2O_3$, $Au/Fe_2O_3$, Cu/ZnO, $CeO_2$, $TiO_2$, $ZrO_2$, $La_2O_3$, $Zn/Fe_2O_3$, and a combination thereof; preferably, selected from Cu—$ZnO/Al_2O_3$, Cu—ZnO—$Ga_2O_3/SiO_2$, Cu—ZnO—$Al_2O_3/ZrO_2$, more preferably selected from Cu—ZnO—$Al_2O_3/ZrO_2$.

In the embodiments wherein a recycle step is performed on at least one second reactor, one or more reverse water-gas shift catalysts, to convert the carbon monoxide and the water present in the one or more second reactors 19 into carbon dioxide and hydrogen that can be recycled into the first reactor 11. The one or more reverse water-gas shift catalysts are preferably located at the end of the bed of the one or more second reactors.

Examples of reverse water-gas shift catalyst are $Fe_2O_3$, $ZnNiFe_2O_4$, Ba—$Fe_3O_3$—$Al_2O_3$—NiO, Cu—Mn spinel oxide, $La_{2-x}Ca_xCuO_4$, oxide supported Cu, $CuO/ZrO_2$, $CeO_2/CuO$, oxide supported Au, Cu—$CeO_2$—$La_2O_3$. The reverse water-gas shift catalyst allows converting the carbon monoxide and the water in the second reactor 19 into carbon dioxide and hydrogen, which are then recovered into the second gaseous effluent 23 and can be recycled into the recycle step (see below).

According to the disclosure, the first and/or second methanol synthesis catalyst comprises a catalyst support providing mechanical support as well as further enhancing the exposure of the active sites to the syngas feedstream 3 or the first gaseous effluent 15, respectively. In such a supported configuration, the amount of the first and/or second methanol synthesis catalyst (represented as weight loading of the first and/or second methanol synthesis catalyst based on the total weight of the supported catalyst) can be in the range of about 0.1 wt. % to about 95 wt. %.

In a preferred embodiment, the first and/or second methanol synthesis catalyst is a calcined catalyst wherein calcination is conducted prior to the step of providing the catalyst composition. The calcination step is advantageously performed at a temperature above 500 K (226.85° C.), preferably above 530 K (256.85° C.), more preferably above 550 K (276.85° C.), even more preferably above 570 K (296.85° C.).

Once calcined, the first and/or second methanol synthesis catalyst displays a crystalline structure observed by X-ray diffraction. Also, the absence of organic and/or nitrogen compounds can be demonstrated by HCN analysis. Such compounds would be derived from the metal precursors, e.g., $In(NO_3)_3 \cdot xH_2O$. Indeed, the non-calcined catalyst would exhibit organic and/or nitrous and/or hydrogen content in its HCN analysis.

For example, the catalyst support of the first and/or second methanol synthesis catalyst comprises at least one selected from silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), zirconium dioxide ($ZrO_2$), titanium dioxide ($TiO_2$), magnesium oxide (MgO), zinc oxide (ZnO), tin oxide ($SnO_2$), carbon black (C), and combinations thereof. Preferably, the catalyst support of the first and/or second methanol synthesis catalyst comprises at least one selected from zinc oxide (ZnO), zirconium dioxide ($ZrO_2$) and titanium dioxide ($TiO_2$) or a combination thereof; and more preferably the catalyst support of the first and/or second methanol synthesis catalyst is or comprises zirconium dioxide. When the catalyst support comprises zirconium dioxide ($ZrO_2$), the zirconium dioxide can be monoclinic, tetragonal, or cubic.

In an embodiment, the catalyst support of the first and/or second methanol synthesis catalyst is zirconium dioxide or a combination of zirconium dioxide with another catalyst support in which zirconium dioxide is comprised in an amount of at least 10 wt. %, preferably at least 50 wt. %, more preferably at least 80 wt. %, and even more preferably at least 90 wt. % based on the total weight of the catalyst support, the other catalyst support is selected from silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), titanium dioxide ($TiO_2$), magnesium oxide (MgO), zinc oxide (ZnO), tin oxide ($SnO_2$), carbon black (C), and combinations thereof; preferably the other catalyst support is selected from zinc oxide (ZnO), titanium dioxide ($TiO_2$), and combinations thereof.

The catalyst support of the first and/or second methanol synthesis catalyst can be porous or non-porous. In some embodiments, the catalyst support of the first and/or second methanol synthesis catalyst is provided in a particulate form of particles having a surface area (i.e., BET surface area) as determined by $N_2$ sorption analysis according to ASTM D3663-03, in the range of about 5 $m^2 \, g^{-1}$ to about 400 $m^2 \, g^{-1}$, such as from 30 $m^2 \, g^{-1}$ to about 200 $m^2 \, g^{-1}$, and/or with a pore volume in the range of about 0.1 $cm^3 g^{-1}$ to about 10 $cm^3 \, g^{-1}$, such as from about 0.2 $cm^3 \, g^{-1}$ to about 5 $cm^3 \, g^{-1}$.

The first and/or second methanol synthesis catalyst can be a calcined supported catalyst and has preferably a surface area (i.e BET surface area) as determined by $N_2$ sorption analysis according to ASTM D3663-03, in the range of about 5 $m^2 g^{-1}$ to about 400 $m^2 \, g^{-1}$, such as from 30 $m^2 \, g^{-1}$ to about 200 $m^2 \, g^{-1}$.

With preference, the first and/or second methanol synthesis catalyst is in the form of particles having an average crystal size of less than 20 nm as determined by X-Ray Diffraction, preferably less than 15 nm, more preferably less than 12 nm, even more preferably less than 10 nm.

The first and/or second methanol synthesis catalyst comprises an active phase and the active phase can be combined with a catalyst support or other support medium through, for example, impregnation, such that the first and/or second methanol synthesis catalyst can be coated on, deposited on, impregnated on or otherwise disposed adjacent to the catalyst support. For example, a supported catalyst can be synthesized by an impregnation step followed by a calcination step. The first and/or second methanol synthesis catalyst can be provided in technical shapes such as extrudates, granules, spheres, monoliths, or pellets and might contain additives such as lubricants, peptizers, plasticizers, porogens, binders, and/or fillers.

In a preferred embodiment, the first and/or second methanol synthesis catalyst comprises at least one metal as a promoter, wherein preferably the first and/or second methanol synthesis catalyst and the at least one metal are deposited on a support. With preference, at least one metal is selected from ruthenium (Ru), rhodium (Rh), palladium (Pd), silver (Ag), osmium (Os), platinum (Pt), copper (Cu), nickel (Ni), cobalt (Co), gold (Au), iridium (Ir), and any combinations thereof; preferably a metal selected from ruthenium (Ru), rhodium (Rh), palladium (Pd), silver (Ag), platinum (Pt), copper (Cu), nickel (Ni), cobalt (Co) and any combinations thereof; more preferably, a metal selected from ruthenium (Ru), rhodium (Rh), palladium (Pd), silver (Ag), platinum (Pt), and any combinations thereof; even more preferably, a metal selected from palladium (Pd) and/or platinum (Pt), and most preferably the metal is palladium (Pd).

In an embodiment, the first and/or second methanol synthesis catalyst is devoid of gold (Au).

With preference, said at least one metal is in an oxidized form.

With preference, the average particle size of the one or more metal phase is less than 5 nm as determined by Scanning Transmission Electronic Microscopy—Energy-Dispersive X-Ray Spectroscopy (STEM-EDX), more preferably less than 4 nm, even more preferably less than 2 nm.

In an embodiment, the first and/or second methanol synthesis catalyst is a calcined supported catalyst and comprises from 0.01 to 10 wt. % of the at least one metal based on the total weight of the calcined supported catalyst.

With preference, the first and/or second methanol synthesis catalyst is a calcined supported catalyst and comprises at least 0.05 wt. % of the at least one metal based on the total weight of the calcined supported catalyst, preferably at least 0.1 wt. %, more preferably at least 0.3 wt. %, even more preferably at least 0.5 wt. %, and most preferably at least 0.7 wt. %.

With preference, the first and/or second methanol synthesis catalyst is a calcined supported catalyst and comprises at most 10.0 wt. % of the at least one metal based on the total weight of the calcined supported catalyst, preferably at most 7.0 wt. %, more preferably at most 5.0 wt. %, even more preferably at most 2.0 wt. %, and most preferably at most 1.0 wt. %.

Before reaction, the first methanol synthesis catalyst can be activated in situ by raising the temperature to at least 270° C. in a flow of a gaseous feedstream for activation selected from inert gases, hydrogen, carbon monoxide, carbon dioxide or a mixture thereof.

Also, before reaction, the second methanol synthesis catalyst can be activated in situ by raising the temperature to at least 180° C. in a flow of a gaseous feed stream for activation selected from inert gases, hydrogen, carbon monoxide, carbon dioxide or a mixture thereof.

The Copper Zinc Oxide Catalyst

It is preferred that the at least one first methanol synthesis catalyst and/or the at least one second methanol synthesis catalyst is or comprises a copper zinc oxide catalyst. For example, said copper zinc oxide catalyst is selected from Cu/ZnO, Cu—ZnO/Al$_2$O$_3$, Cu—ZnO—Ga$_2$O$_3$/SiO$_2$, Cu—ZnO—Al$_2$O$_3$/ZrO$_2$ and any mixture thereof; preferably said copper zinc oxide catalyst is or comprises Cu—ZnO—Al$_2$O$_3$/ZrO$_2$. Before step (c) and/or step (e), said copper zinc oxide catalyst can be activated, preferably by reduction with hydrogen. Said copper zinc oxide catalyst is advantageously prepared by co-precipitation. For example, said copper zinc oxide catalyst is an activated supported catalyst and/or has a surface area in the range of about 5 m$^2$ g$^{-1}$ to about 400 m$^2$ g$^{-1}$, such as from 30 m$^2$ g$^{-1}$ to about 200 m$^2$ g$^{-1}$ as determined according to N$_2$ sorption analysis according to ASTM D3663-03.

The Indium Oxide Catalyst

For example, the first methanol synthesis catalyst is an indium oxide catalyst since this catalyst provides better resistance to a large amount of carbon dioxide than other methanol synthesis catalysts. As the indium oxide catalyst is relatively more expensive than other methanol synthesis catalysts, the configuration of the installation of the present disclosure is advantageous, since, in the first reactor, the indium oxide catalyst can convert the syngas into methanol and water under CO$_2$-rich conditions and at elevated temperature and therefore preparing the first gaseous effluent to contact a second catalytic composition with a lesser amount of CO$_2$. This allows using different methanol synthesis catalysts in the second catalytic composition that are more affordable. Furthermore, the lower CO$_2$/CO molar ratio at the input of the second reactor 19 allows for using a temperature which is lowered than the first temperature conditions.

For example, the indium oxide catalyst is under the form of In$_2$O$_3$.

According to the disclosure, the indium oxide catalyst comprises a catalyst support providing mechanical support as well as further enhancing the exposure of the active sites to the syngas feedstream 3. In such a supported configuration, the amount of the indium oxide catalyst (represented as weight loading of the catalyst based on the total weight of the supported catalyst) can be in the range of about 0.1 wt. % to about 95 wt. %.

In a preferred embodiment, said first catalytic composition 9 comprising at least one indium oxide catalyst is calcined before the step of the step of providing said catalyst. The calcination step is advantageously performed at a temperature above 500 K (226.85° C.), preferably above 530 K (256.85° C.), more preferably above 550 K (276.85° C.), even more preferably above 570 K (296.85° C.).

Once calcined, the indium oxide catalyst displays a crystalline structure observed by X-ray diffraction. Also, the absence of organic and/or nitrogen compounds can be demonstrated by HCN analysis. Such compounds would be derived from the metal precursors, e.g., In(NO$_3$)$_3$·xH$_2$O. Indeed, the non-calcined catalyst would exhibit organic and/or nitrous and/or hydrogen content in its HCN analysis.

For example, the catalyst support of the indium oxide catalyst comprises at least one selected from silica (SiO$_2$), alumina (Al$_2$O$_3$), gallium oxide (Ga$_2$O$_3$), cerium oxide (CeO$_2$), vanadium oxide (V$_2$O$_5$), chromium oxide (Cr$_2$O$_3$), zirconium dioxide (ZrO$_2$), titanium dioxide (TiO$_2$), magnesium oxide (MgO), zinc oxide (ZnO), tin oxide (SnO$_2$), carbon black (C), and combinations thereof. Preferably, the catalyst support of the indium catalyst comprises at least one selected from zinc oxide (ZnO), zirconium dioxide (ZrO$_2$) and titanium dioxide (TiO$_2$) or a combination thereof; and more preferably the catalyst support of the indium oxide catalyst is or comprises zirconium dioxide. When the catalyst support comprises zirconium dioxide ($ZrO_2$), the zirconium dioxide can be monoclinic, tetragonal, or cubic.

In an embodiment, the catalyst support of the indium oxide catalyst is zirconium dioxide or a combination of zirconium dioxide with another catalyst support in which zirconium dioxide is comprised in an amount of at least 10 wt. %, preferably at least 50 wt. %, more preferably at least 80 wt. %, and even more preferably at least 90 wt. % based on the total weight of the catalyst support, the other catalyst support is selected from silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), titanium dioxide ($TiO_2$), magnesium oxide (MgO), zinc oxide (ZnO), tin oxide ($SnO_2$), carbon black (C), and combinations thereof; preferably the other catalyst support is selected from zinc oxide (ZnO), titanium dioxide ($TiO_2$), and combinations thereof.

The catalyst support of the indium oxide catalyst can be porous or non-porous. In some embodiments, the catalyst support of the indium oxide catalyst is provided in a particulate form of particles having a surface area (i.e., BET surface area) as determined by $N_2$ sorption analysis according to ASTM D3663-03, in the range of about 5 $m^2$ $g^{-1}$ to about 400 $m^2$ $g^{-1}$, such as from 30 $m^2$ $g^{-1}$ to about 200 $m^2$ $g^{-1}$, and/or with a pore volume in the range of about 0.1 $cm^3 g^{-1}$ to about 10 $cm^3$ $g^{-1}$, such as from about 0.2 $cm^3$ $g^{-1}$ to about 5 $cm^3$ $g^{-1}$.

The indium oxide catalyst can be a calcined supported catalyst and has preferably a surface area (i.e BET surface area) as determined by $N_2$ sorption analysis according to ASTM D3663-03, in the range of about 5 $m^2 g^{-1}$ to about 400 $m^2$ $g^{-1}$, such as from 30 $m^2$ $g^{-1}$ to about 200 $m^2$ $g^{-1}$.

With preference, the indium oxide catalyst is in the form of particles having an average crystal size of less than 20 nm as determined by X-Ray Diffraction, preferably less than 15 nm, more preferably less than 12 nm, even more preferably less than 10 nm.

The indium oxide catalyst comprises an active phase and the active phase can be combined with a catalyst support or other support medium through, for example, impregnation, such that the indium oxide catalyst can be coated on, deposited on, impregnated on or otherwise disposed adjacent to the catalyst support. For example, a supported catalyst can be synthesized by an impregnation step followed by a calcination step. The indium oxide catalyst can be provided in technical shapes such as extrudates, granules, spheres, monoliths, or pellets and might contain additives such as lubricants, peptizers, plasticizers, porogens, binders, and/or fillers.

In a preferred embodiment, the indium oxide catalyst comprises at least one metal as a promoter, wherein preferably both indium oxide and the at least one metal are deposited on a support. With preference, at least one metal is selected from ruthenium (Ru), rhodium (Rh), palladium (Pd), silver (Ag), osmium (Os), platinum (Pt), copper (Cu), nickel (Ni), cobalt (Co), gold (Au), iridium (Ir), and any combinations thereof; preferably a metal selected from ruthenium (Ru), rhodium (Rh), palladium (Pd), silver (Ag), platinum (Pt), copper (Cu), nickel (Ni), cobalt (Co) and any combinations thereof; more preferably, a metal selected from ruthenium (Ru), rhodium (Rh), palladium (Pd), silver (Ag), platinum (Pt), and any combinations thereof; even more preferably, a metal selected from palladium (Pd) and/or platinum (Pt), and most preferably the metal is palladium (Pd).

In an embodiment, the indium oxide catalyst is devoid of gold (Au).

With preference, said at least one metal is in an oxidized form.

With preference, the average particle size of the one or more metal phase is less than 5 nm as determined by Scanning Transmission Electronic Microscopy—Energy-Dispersive X-Ray Spectroscopy (STEM-EDX), more preferably less than 4 nm, even more preferably less than 2 nm.

In an embodiment, the indium oxide catalyst is a calcined supported catalyst and comprises from 0.01 to 10 wt. % of the at least one metal based on the total weight of the calcined supported catalyst.

With preference, the indium oxide catalyst is a calcined supported catalyst and comprises at least 0.05 wt. % of the at least one metal based on the total weight of the calcined supported catalyst, preferably at least 0.1 wt. %, more preferably at least 0.3 wt. %, even more preferably at least 0.5 wt. %, and most preferably at least 0.7 wt. %.

With preference, the indium oxide catalyst is a calcined supported catalyst and comprises at most 10.0 wt. % of the at least one metal based on the total weight of the calcined supported catalyst, preferably at most 7.0 wt. %, more preferably at most 5.0 wt. %, even more preferably at most 2.0 wt. %, and most preferably at most 1.0 wt. %.

Before reaction, the indium oxide catalyst of the first catalytic composition 9 can be activated in situ by raising the temperature to at least 270° C. in a flow of a gaseous feedstream for activation selected from inert gases, hydrogen, carbon monoxide, carbon dioxide or a mixture thereof.

Also, before reaction, the indium oxide catalyst of the second catalytic composition 17 if this less preferred option is envisioned, can be activated in situ by raising the temperature to at least 180° C. in a flow of a gaseous feed stream for activation selected from inert gases, hydrogen, carbon monoxide, carbon dioxide or a mixture thereof.

The Process for Methanol Synthesis and the Installation to Perform the Process

The process according to the disclosure comprises the following steps:
  a) providing a syngas feedstream 3 comprising hydrogen and carbon oxides, wherein the carbon oxides are selected from carbon dioxide or a mixture of carbon dioxide and carbon monoxide provided that the molar ratio of carbon dioxide over carbon monoxide in the mixture is equal to or greater than 1.0 and that said syngas feedstream comprises at least 12.0 mol % of $CO_2$ based on the total molar content of said syngas feedstream;
  b) providing a first catalytic composition 9 that comprises at least one first methanol synthesis catalyst;
  c) putting into contact said syngas feedstream 3 with said first catalytic composition 9 under first reaction conditions comprising first temperature conditions, to provide a first gaseous effluent 15 and optionally a first liquid effluent;
  d) providing second catalytic composition 17 that comprises at least one second methanol synthesis catalyst wherein said at least one second methanol synthesis catalyst is the same or different from said one first methanol synthesis catalyst;
  e) putting into contact at least a part of said first gaseous effluent 15 with said second catalytic composition 17 under second reaction conditions comprising second temperature conditions, to provide a second gaseous effluent 23 and a second liquid effluent 21;

f) recovering methanol from one or more selected from the first gaseous effluent and the second gaseous effluent 23;

wherein the first temperature conditions are at least 270° C. and wherein the second temperature conditions are lower than the first temperature conditions and second temperature conditions are ranging between 180° C. and 250° C.

The process can be carried out in a gaseous phase or a liquid phase. The solvent that can be used for the reaction in liquid phase includes hydrocarbons and other solvents which are preferably insoluble or only sparingly soluble in water. Preferably, the process is carried out in a gaseous phase. The below description is related to the preferred embodiments wherein the process is carried out in a gaseous phase.

The process and the installation will be further described simultaneously by reference to FIG. 1.

The installation 1 to perform the process according to the disclosure comprises one first reactor 11 and at least one second reactor 19 arranged in series. The first reactor 11 is loaded with a first catalytic composition 9 that comprises at least one first methanol synthesis catalyst, for example, an indium oxide catalyst or preferably a copper zinc oxide catalyst, and is arranged upstream of the one or more second reactors 19 which are loaded with a second catalytic composition 17 that comprises at least one second methanol synthesis catalyst, for example, one or more methanol synthesis catalysts which are different from an indium oxide catalyst or preferably different from a copper zinc oxide catalyst, respectively. According to the disclosure, each reactor (11, 19) is provided with a device for heating the reactor; and with preference with:

a temperature sensor and controller for detecting and controlling the temperature of the reactor at a reaction temperature; and/or flow controllers to control the rate of the gaseous stream to the reactor; and/or a pressure controller to control the reactor pressure.

With preference, the one or more first and/or the one or more second reactors (11, 19) are fixed-bed reactors or fluidized-bed reactors comprising at least one catalytic bed. Such reactors are well-known from the person skilled in the art and for instance described in EP2257366 or in U.S. Pat. No. 7,279,138.

For example, the first reactor 11 comprising said at least one first catalytic composition 9 forms a first catalytic bed and the temperature within said first reactor 11 is the temperature at the exit of said first catalytic bed.

For example, the at least one subsequent reactor 19 comprising said at least one second catalytic composition 17 forms at least one subsequent catalytic bed and the temperature within said at least one subsequent reactor 19 is the temperature at the exit of each of one or more subsequent catalytic beds.

A syngas feedstream 3 is provided. The syngas feedstream 3 comprises hydrogen and carbon oxides being a mixture of carbon monoxide and/or carbon dioxide. With preference, the syngas feedstream 3 comprises more than 3.0 mol % of $CO_2$ based on the total molar content of the syngas feedstream 3. The syngas feedstream 3 is provided to the first reactor 11 either directly or after having been mixed with a recycled gaseous stream 37 through a mixing device 5. With preference, the gaseous feedstream resulting from the mixture of the syngas feedstream 3 and the recycle stream 37 still comprises more than 3.0 mol % of $CO_2$ based on the total molar content of the gaseous feedstream. The syngas feedstream 3 or the gaseous feedstream resulting from the mixture of the syngas feedstream 3 and the recycle stream 37 is introduced to the first reactor by a line 7.

In step (c) of the process, the syngas feedstream (3, 7) entering the first reactor 11 is put into contact with a first catalytic composition 9 comprising at least one first methanol synthesis catalyst, as defined above, under first reaction conditions.

It is advantageous that the first temperature conditions are ranging between 270° C. and 350° C., preferably between 275° C. and 345° C., or between 280° C. and 340° C., more preferably between 285° C. and 340° C.

It is also preferred that said first reaction conditions comprise a reaction pressure of at least 0.5 MPa, preferably at least 1.0 MPa, more preferably at least 2.0 MPa, even more preferably at least 3.0 MPa, and most more preferably at least 4.0 MPa. For example, the pressure is comprised between 0.5 and 12.0 MPa, preferably between 1.0 and 9.0 MPa, more preferably between 1.5 and 8.0 MPa.

In a preferred embodiment, said first reaction conditions comprise a gas hourly space velocity (GHSV) of the syngas feedstream 3, or of the gaseous feedstream resulting from the mixture of the syngas feedstream 3 and the recycle feedstream 37, in the range of 1,000 to 100,000 $h^{-1}$, preferably of 2,000 to 70,000 $h^{-1}$, more preferably of 5,000 to 60,000 $h^{-1}$, and more preferably of 8,000 to 50,000 $h^{-1}$.

In an embodiment, the process is carried out with a stable performance of the first catalyst composition for activity and selectivity during more than 100 h, preferably more than 1,000 h, more preferably more than 10,000 h, and even more preferably more than 100,000 h without the need of reactivation or replacement of the first methanol synthesis catalyst.

A first gaseous effluent 15 is produced in the first reactor 11. Said first gaseous effluent 15 comprises methanol, CO, water and the remaining unreacted $CO_2$ and $H_2$ from the syngas feed stream 3 or from the gaseous feedstream resulting from the mixture of the syngas feedstream 3 and the recycle stream 37. At least of part of said first gaseous effluent 15 is directed into the one or more second reactors 19.

With preference, the first gaseous effluent 15 which is directed into the second reactor 19, comprises at most 18 mol % of $CO_2$ based on the total molar content of the first gaseous effluent 15. This is an optimal value that can be accepted by most of the commercial methanol synthesis catalysts. The $CO_2/CO$ molar ratio in the first effluent 15 which is directed into the second reactor 19, is below 3, preferably below 2, more preferably below 1. In all cases, the $CO_2/CO$ molar ratio in the first effluent 15, is below the $CO_2/CO$ molar ratio in the syngas feedstream 3 or in the gaseous feedstream resulting from the mixture of the syngas feedstream 3 and the recycle feedstream 37.

In step (e) of the process, at least a part or all of the first gaseous effluent 15, is introduced to the second reactor 19 and put into contact with the second catalytic composition 17 under second reaction conditions to provide a second gaseous effluent 23 and optionally a second liquid effluent 21.

In a preferred embodiment the second reaction conditions comprise second temperature conditions between 180° C. and 250° C., preferably between 180° C. and below 250° C.; preferably between 185° C. and 245° C.; more preferably between 190° C. and 240° C., even more preferably between 200° C. and 235° C.

The second temperature conditions are advantageously the start-of-run temperature conditions and/or the temperature at the exit of the catalytic bed of each reactor.

It is also preferred that said second reaction conditions comprise second pressure conditions of at least 0.5 MPa, preferably at least 1.0 MPa, more preferably at least 2.0 MPa, even more preferably at least 3.0 MPa, most more preferably at least 4.0 MPa and even most preferably at least 5.0 MPa. For example, the pressure is comprised between 0.5 and 12.0 MPa, preferably between 1.0 and 9.0 MPa; more preferably between 1.5 and 8.0 MPa.

In a preferred embodiment, said second reaction conditions comprises a gas hourly space velocity (GHSV) of said first gaseous effluent 15 in the range of 1,000 to 100,000 $h^{-1}$, preferably of 2,000 to 70,000 $h^{-1}$, more preferably of 5,000 to 60,000 $h^{-1}$, and more preferably of 15,000 to 50,000 $h^{-1}$.

Advantageously, the first and second pressure conditions are similar. A slight drop can be observed between the first and the second pressure conditions. It is also advantageous that the gas hourly space velocity of the syngas feedstream 3 and the gas hourly space velocity of the first gaseous effluent are identical.

Therefore, the process is carried out with a stable performance of the second catalytic composition 19 comprising at least one second methanol synthesis catalyst, with an activity and a selectivity during more than 100 h, preferably more than 1,000 h, more preferably more than 10,000 h, and even more preferably more than 100,000 h without the need of reactivation or replacement of the one or more second methanol synthesis catalysts. This is the main interest of the process of the present disclosure.

The second liquid effluent 21 can be optionally collected and comprises a mixture of methanol and water.

The second gaseous effluent 23 can be directed to a (final) gas/liquid separator 27, with an optional step of cooling performed by a cooling device 26.

A recycle step can be performed, according to which the second gaseous effluent 23 is recycled to be put into contact with the first catalytic composition 9 again. Therefore, the second gaseous effluent 23 exiting the one or more second reactors 19 is recycled to the inlet of the first reactor 11 through a dedicated line (not shown).

Within the cooling device 26, the second gaseous effluent 23 is preferably cooled down to a temperature comprised between 20° C. and 60° C., more preferably between 25° C. and 55° C., even more preferably between 30° C. and 50° C.

The (final) gas/liquid separator 27 is configured to separate the second gaseous effluent 23 into a liquid effluent 21 and a third gaseous effluent 31. The third liquid effluent 29 can be collected and comprises a mixture of methanol and water. The third gaseous effluent 31 is optionally further separated by a splitter 33 into a recycle stream 37 and a purge stream 35.

The recycle step according to which the second gaseous effluent 23 is recycled to be put into contact with the first catalytic composition 9 again is advantageously performed downstream of the (final) gas/liquid separator 27 as shown on FIG. 1, namely after having recovered the liquid effluent 21 comprising a mixture of methanol and water from the second gaseous effluent 23.

Figure 2:
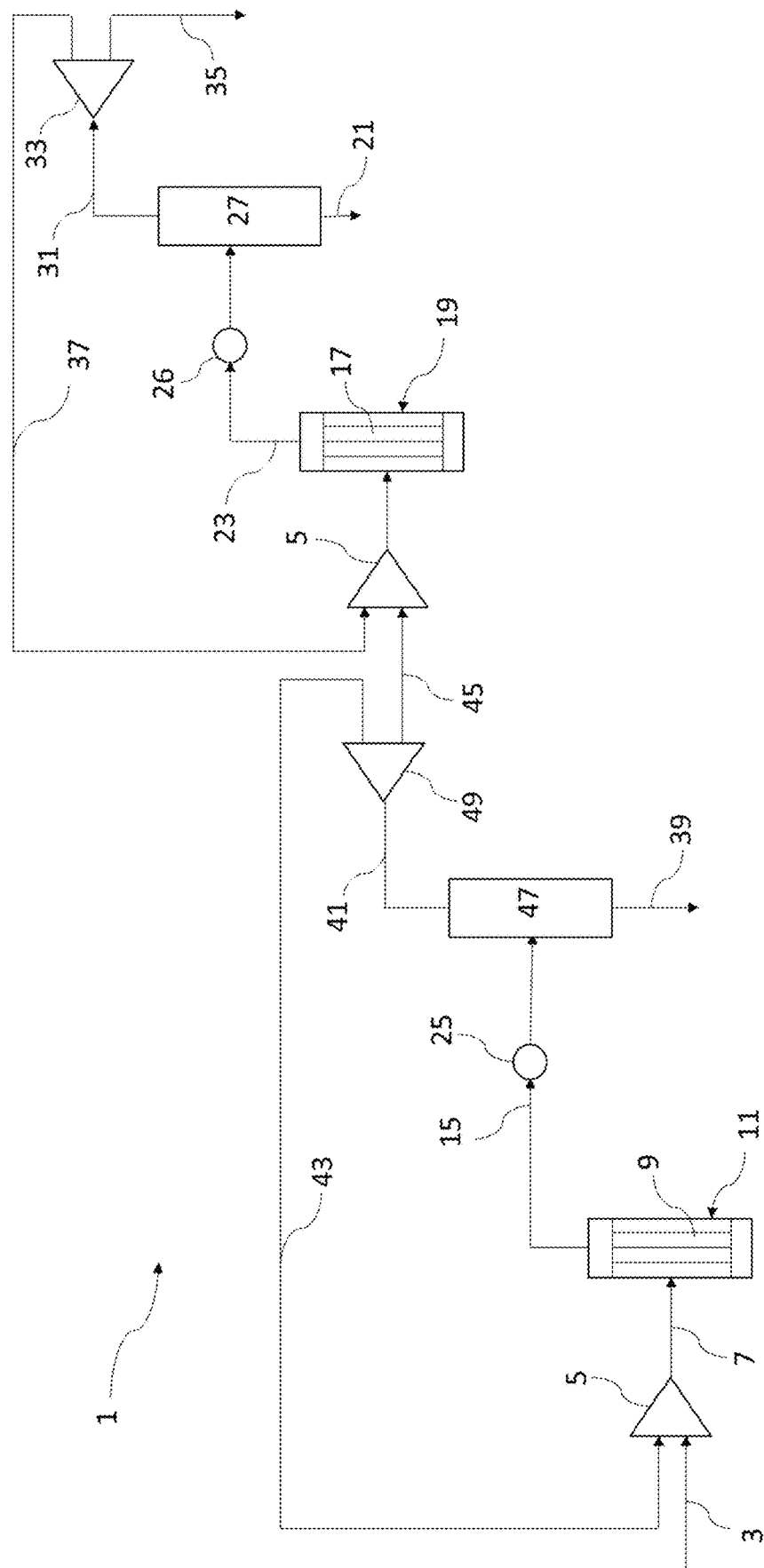
FIG. 2 illustrates a second embodiment of an installation to conduct the process according to the disclosure.

Methanol and Water can Thus be Recovered from any of the First 15, Second 23 and Third 31 Gaseous Effluent by Liquid-Gas Separation Another embodiment of the installation and process of the disclosure is provided in FIG. 2. In this embodiment, the first gaseous effluent 15, exiting the first reactor 11, is directed to a gas/liquid separator 47, after having been optionally cooled down in a cooling device 25. Said first gaseous effluent 15 is preferably cooled down to a temperature comprised between 20° C. and 60° C., more preferably between 25° C. and 55° C., even more preferably between 30° C. and 50° C.

The first gaseous effluent 15 can be directed to a first (intermediate) gas/liquid separator 47, with an optional step of cooling performed by a cooling device 25.

The first (intermediate) gas/liquid separator 47, disposed between the first reactor 11 and the second reactor 19, is configured to separate the first gaseous effluent 15 into a fourth liquid effluent 39 and a fourth gaseous effluent 41. The fourth liquid effluent 39 can be collected and comprises a mixture of methanol and water. The fourth gaseous effluent 41 is optionally further separated by a splitter 49 into a $CO_2$-enriched gaseous stream 43 and a CO-enriched gaseous stream 45.

A first-reactor-recycle step can be performed, according to which the $CO_2$-enriched gaseous stream 43 is recycled to be put into contact with the first catalytic composition 9 again by being for example mixed with the syngas feedstream 3. Therefore, a part of the first gaseous effluent exiting the first reactor 11 is recycled to the inlet of the first reactor 11 through a dedicated line.

The CO-enriched gaseous stream 45 can be provided to the second reactor 19 either directly or after having been mixed to a recycle gaseous stream 37 through a mixing device 5 (see below, in relation with the second-reactor-recycle step).

Once the second gaseous effluent 23 exits the second reactor 19, it can be directed to a second (final) gas/liquid separator 27, with an optional step of cooling performed by a cooling device 26.

A second-reactor-recycle step can be performed at this level, according to which a part of the second gaseous effluent 23 is recycled to be put into contact with the second catalytic composition 19 again. Therefore, a part of the second gaseous effluent 23 exiting the one or more second reactors 19 is recycled to the inlet of the one or more second reactors 19 through a dedicated line. The second (final) gas/liquid separator 27 is configured to separate the second gaseous effluent 23 into a liquid effluent 21 and a third gaseous effluent 31. The liquid effluent 21 can be collected and comprises a mixture of methanol and water. The third gaseous effluent 31 is optionally further separated by a splitter 33 into a recycle stream 37 and a purge stream 35. The second-reactor-recycle step is therefore accomplished when the recycle stream 37 is redirected to the mixing device 5 upstream of the second reactor 19 or directly to the second reactor 19.

In the example illustrated in FIG. 2, said first-reactor-recycle step and said second-reactor-recycle step are performed concomitantly (see cases 9a and 9b in the examples below).

Figure 3:
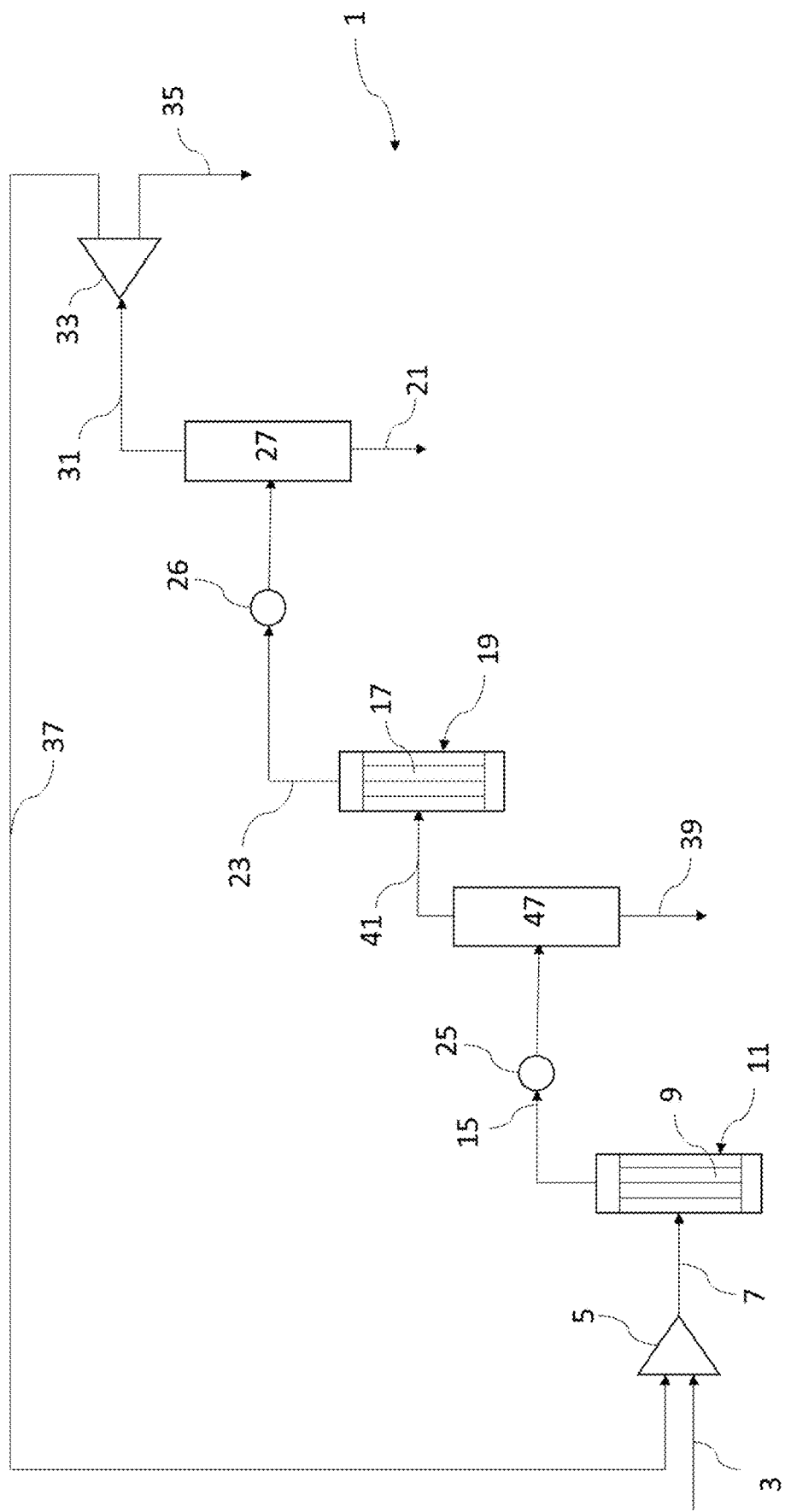
FIG. 3 illustrates a third embodiment of an installation to conduct the process according to the disclosure.

Finally, FIG. 3 is the illustration of a configuration according to the preferred embodiment of the disclosure, showing an installation having a first (intermediate) gas/liquid separator 47 disposed in between the first reactor 11 and the second reactor 19, with a cooling device 25 upstream to said first gas/liquid separator 47; and a second (final) gas/liquid separator 27 disposed downstream of the second reactor 19, with a cooling device 26 upstream to said second gas/liquid separator 27. The second gas/liquid separator 27 is useful for generating the third gaseous effluent 31 which can be then directed into the splitter 33 for performing the recycling step of the second gaseous effluent 23, from the second reactor 19 to the first reactor 11.

Test and Determination Methods

Powder XRD analysis was performed using a PANalytical X'Pert Pro MPD instrument, utilizing Cu-Kα radiation ($\lambda$=0.1541 nm), an angular step size of 0.05° 2θ and a counting time of 12 seconds per step. The average crystal size of $In_2O_3$ was estimated from the (222) reflection applying the Scherrer equation.

XPS analysis was performed in a Physical Electronics Instruments Quantum 2000 spectrometer using monochromatic Al Kα radiation generated from an electron beam operated at 15 kV and 32.3 W. The spectra were collected under ultra-high vacuum conditions (residual pressure=5× $10^{-8}$ Pa) at pass energy of 46.95 eV. All spectra were referenced to the C 1s peak at 284.8 eV. Although samples were extracted from the reactor in inert atmosphere, the design of the instrument made a brief (<2 min) exposure to air upon sample introduction unavoidable.

STEM-EDX measurements were performed using a Talos F200X instrument operated at 200 kV and equipped with an FEI SuperX detector.

The metal composition of the calcined samples was determined by inductively coupled plasma-optical emission spectrometry (ICP-OES) using a Horiba Ultra 2 instrument equipped with a photomultiplier tube detector. Before analysis, the catalysts were dissolved in aqua regia and the resulting solutions were diluted with twice-distilled water.

Specific surface area and pore volume were determined from the sorption isotherm of $N_2$ at 77 K using a Micromeritics TriStar II analyzer. The Brunauer-Emmett-Teller (BET) method was applied for calculating the specific surface area according to ASTM D3663-03 and the volume of gas adsorbed at saturation pressure was used to determine the pore volume.

Temperature-programmed reduction with $H_2$ ($H_2$-TPR) was carried out at the reaction pressure (5.0 MPa) in a Micromeritics AutoChem HP II analyser. 100 mg of catalyst was used for each analysis. A drying step in 100 $cm^3_{STP}$ $min^{-1}$ Argon was carried out at 0.1 MPa between 303-393 K, at a heating rate of 5 K $min^{-1}$ and a hold time of 60 min at the final temperature. Thereafter, the temperature was lowered to 183 K at a rate of 5 K $min^{-1}$ and reduction with 5% $H_2$ in Argon at a flow rate of 50 $cm^3_{STP}$ $min^{-1}$ was carried out between 183-1103 K, with a heating rate of 5 K $min^{-1}$, at a pressure of 5.0 MPa, and a hold time of 30 min at the final temperature.

Example

The advantages of the present disclosure are illustrated by the following examples. However, it is understood that the disclosure is no means limited to the specific examples.

Example 1: Synthesis of an Indium Oxide Catalyst Impregnated on $ZrO_2$

The materials used were an indium salt, i.e., indium (Iii) nitrate hydrate ($In(NO_3)_3 \cdot xH_2O$, Alfa Aesar, 99.99%); a mainly monoclinic (Saint-Gobain NorPro, SZ 31164) or a purely cubic (synthesized according to the preparation procedure described below) $ZrO_2$ catalyst support, and deionized water.

The $ZrO_2$ catalyst support (Saint-Gobain NorPro, SZ 31164, extrudates having diameter 3-4 mm and length 4-6 mm) with monoclinic structure (with ~5 wt. % cubic phase) was used, having the following specifications (before mortar crushing):

a specific surface area of 85 $m^2$ $g^{-1}$ ($N_2$ sorption analysis)
a pore volume of 0.29 $cm^3$ $g^{-1}$ ($N_2$ sorption analysis)

Synthesis of the cubic $ZrO_2$ catalyst support: 5.21 g of zirconyl nitrate hydrate ($ZrO(NO_3)_2 \cdot xH_2O$, Acros Organics, 99.5%) was dissolved in 500 ml of deionized water under stirring. 31 ml of ethylenediamine (Fluka, 99.5%) was added dropwise. The slurry was stirred for a further 30 min and then it was refluxed for 6 h. The obtained solution was filtered and the precipitate was washed with 2l of deionized water. After drying at 338 K (64.85° C.) in the static air, the resulting the material was calcined in static air at 873 K (599.85° C.) for 2 h with a heating rate of 2 K $min^{-1}$.

Preparation of the supported catalysts (11 wt. % $In_2O_3$ loading): 0.76 g of indium salt was dissolved in a mixture of 70 ml of ethanol absolute (Sigma-Aldrich, 99.8%) and 24 ml of deionized water under stirring. 2 g of either crushed as-received monoclinic or as-prepared cubic zirconium dioxide (both sieve fraction<0.075 mm) were added to the solution, which was mixed by a magnetic stirrer for 5 h. The solvent was removed in a rotary evaporator at 333 K (59.85° C.). The resulting material was dried at 338 K (64.85° C.) in static air overnight and finally calcined in static air at 573 K (299.85° C.) for 3 h applying a heating rate of 5 K $min^{-1}$.

The produced catalyst was used in a methanol synthesis reaction.

The below Table 1 compares the results for STY, selectivity, and $CO_2$ conversion obtained for the catalyst of the disclosure compared to other catalysts in prior art studies. Reaction conditions: T=573 K, P=5 MPa, GHSV=21,000 $h^1$, molar ratio $H_2$:$CO_2$=4:1.

TABLE 1

| Catalyst | T[K] | P[MPa] | STY(*) | $S_{MeOH}$[%] | $X_{CO_2}$[%] | Ref |
|---|---|---|---|---|---|---|
| $In_2O_3$/$ZrO_2$ (monoclinic) | 573 (299.85° C.) | 5.0 | 0.321 | 99.9 | 5.6 | [1] |
| $In_2O_3$/$ZrO_2$ (cubic) | 573 (299.85° C.) | 5.0 | 0.330 | 99.9 | 5.8 | [1] |
| Cu—ZnO—$Ga_2O_3$/$SiO_2$ | 543 (269.85° C.) | 2.0 | 0.349 | 99.5 | 5.6 | [2] |
| Au—ZnO—$ZrO_2$ | 493 (219.85° C.) | 8.0 | 0.019 | 99.9 | 2.0 | [3] |
| Ag—ZnO—$ZrO_2$ | 493 (219.85° C.) | 8.0 | 0.015 | 97.0 | 2.0 | [3] |
| Pd—ZnO/CNT | 523 (249.85° C.) | 3.0 | 0.037 | 99.6 | 6.3 | [4] |
| Cu/TaC | 553 (279.85° C.) | 6.0 | 0.042 | 18.2 | 1.4 | [5] |

TABLE 1-continued

| Catalyst | T[K] | P[MPa] | STY(*) | $S_{MeOH}$[%] | $X_{CO_2}$[%] | Ref |
|---|---|---|---|---|---|---|
| $LaCr_{0.5}Cu_{0.5}O_3$ | 523 (249.85° C.) | 2.0 | 0.314 | 90.8 | 10.4 | [6] |

*STY given in $g_{MeOH}$ $h^{-1}$ $g_{cat}^{-1}$

[1] WO2017/118572 or WO2017/118573
[2] Toyir, J.; Ramírez de la Piscina, P.; Fierro, J. L. G.; Homs, N.; *Appl. Catal., B* 2001, 29, 207-215.
[3] Słoczyński, J.; Grabowski, R.; Kozłowska, A.; Olszewski, P.; Stoch, J.; Skrzypek, J.; Lachowska, M.; *Appl. Catal., A* 2004, 278, 11.
[4] Liang, X.-L.; Dong, X.; Lin, G.-D.; Zhang, H.-B.; *Appl. Catal., B* 2009, 88, 315-322.
[5] Dubois, J.-L.; Sayama, K.; Arakawa, H.; *Chem. Lett.* 1992, 21, 5-8.
[6] Jia, L.; Gao, J.; Fang, W.; Li, Q.; *Catal. Commun.* 2009, 10, 2000-2003.

Figure 4:
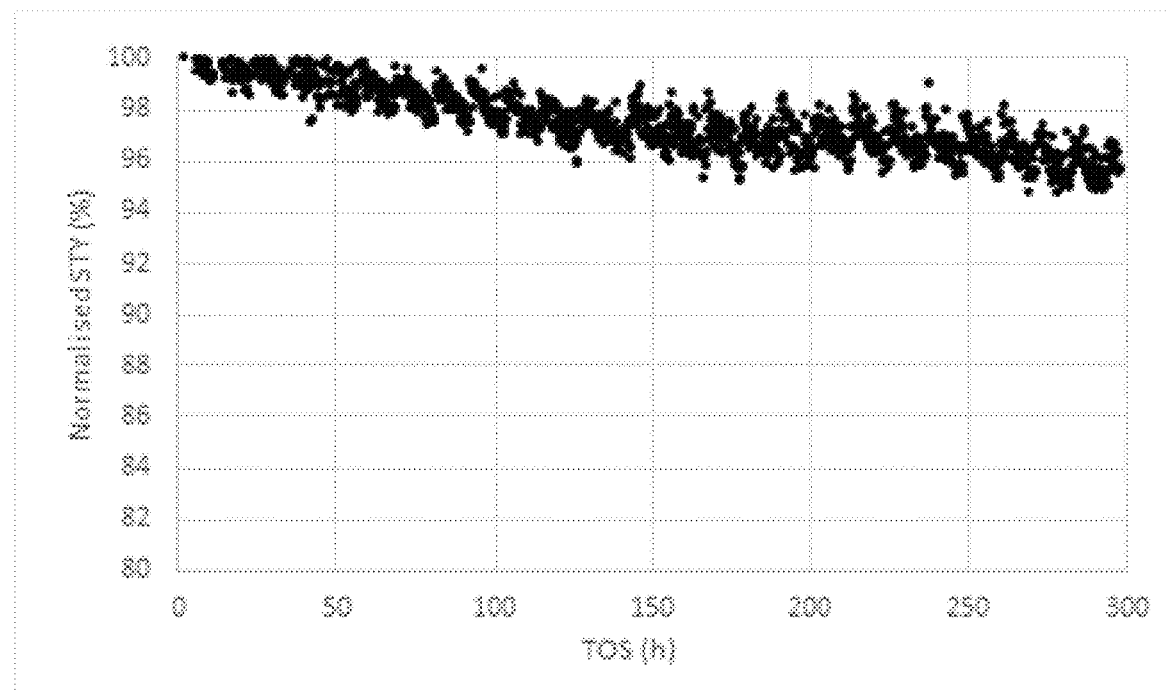
FIG. 4 illustrates the stability of a deposition precipitation palladium-indium oxide-zirconia catalyst ($Pd\text{—}In_2O_3/ZrO_2$).

Example 2: Comparison of the Stability of the First Catalytic Composition 9 Comprising a First Methanol Synthesis Catalyst which is an Indium Oxide Catalyst and the Second Catalytic Composition 17 Comprising One Second Methanol Synthesis Catalyst which is Different than the First Methanol Synthesis Catalyst in a Feedstream Containing $CO_2$ The reactor was loaded with 50 mg of indium oxide-based catalyst with a particle size of 100-125 μm, which was diluted in 50 mg of $TiO_2$ (100-125 μm) and heated from ambient temperature to 280° C. (5° C. $min^{-1}$) at 5 bar under a He flow. After 3 h at 280° C., the pressure was raised to 50 bar in the same stream, which typically took 20 min. Then, the gas flow was switched to the reactant mixture corresponding to a weight hourly space velocity (WHSV) of 48,000 $cm^3$ $h^{-1}$ $g_{cat}^{-1}$ with a $H_2:CO_2$ ratio of 4. A 20 mol % CH/in He was used as an internal standard by injecting a constant flow after the reactor outlet. Tests were carried out up to 300 h time-on-stream. See FIG. 4.

Example 3: Synthesis of an Indium Oxide Catalyst Comprising a Promoter Comprising a Metal Wet Impregnation (WI)

To obtain 9.5 wt. % $In_2O_3$ and 0.5 wt. % Pd on $ZrO_2$, $In(NO_3)_3 \cdot xH_2O$ (0.821 g, Sigma-Aldrich, 99.99%) and $Pd(NO_3)_2 \cdot xH_2O$ (0.014 g, Sigma-Aldrich, >99.99% metals basis) were placed in a 250-$cm^3$ round-bottom flask and dissolved in deionized water (100 $cm^3$). Then $ZrO_2$ (3.00 g, Alfa Aesar, 99.9% metals basis excluding Hf) was added and the slurry was stirred at room temperature for 30 min. The water was then removed using a rotary evaporator (100 rpm, 313 K, 8 kPa, ca. 90 min) and the sample was further dried in a vacuum oven (1.5 kPa, 323 K, ca. 90 min). Thereafter the sample was calcined at 573 K (2 K $min^{-1}$) for 3 h static air.

Coprecipitation (CP)

To obtain 9.9 wt. % $In_2O_3$ and 0.1 wt. % Pd on $ZrO_2$, $In(NO_3)_3 \cdot xH_2O$ (0.57 g), $Pd(NO_3)_2 \cdot xH_2O$ (0.01 g), and zirconyl nitrate solution (9.67 g, Sigma-Aldrich, 35 wt. % in dilute nitric acid) were placed with 70 $cm^3$ of deionized water in a 250-$cm^3$ round-bottom flask. A 10 wt. % $Na_2CO_3$ solution was prepared by dissolving $Na_2CO_3$ (5.0 g, Merck, >99%) in deionized water in a 50-$cm^3$ volumetric flask. 33.9 $cm^3$ of the $Na_2CO_3$ solution were then added drop-wise to the mixture until a pH of 9.2 was reached. The slurry was aged at room temperature for 60 min, then quenched with deionized water (70 $cm^3$), thereafter the solid was separated by high-pressure filtration and washed with deionized water (3 times, 500 $cm^3$ each time). The solid was then dried in a vacuum oven (1.5 kPa, 323 K, 90 min) and calcined at 573 or 773 K for 3 h (2 K $min^{-1}$) in static air.

Sol-Gel Synthesis (SG)

To obtain 9.5 wt. % $In_2O_3$ and 0.5 wt. % Pd on $ZrO_2$, $In(NO_3)_3 \cdot xH_2O$ (0.55 g), $Pd(NO_3)_2 \cdot xH_2O$ (0.02 g), and zirconyl nitrate solution (9.65 g, 35 wt. % in dilute nitric acid) were placed with nitric acid (0.38 g, Fisher Scientific UK, 65%) and deionized water (3.65 $cm^3$) in a 250-$cm^3$ round-bottom flask and stirred at ambient temperature until the dissolution of all solids was observed by eye. A 66.7 wt. % citric acid solution, prepared by dissolving citric acid (1.00 g, Sigma-Aldrich, >98%) in 0.5 $cm^3$ deionized water, was added dropwise to the zirconia mixture. Excess water was removed by evaporation at ambient pressure and 333 K over 3 h, yielding a highly viscous gel. The gel was dried to a powder in a vacuum oven (1.5 kPa, 323 K) and calcined in a tubular oven under a stream (ca. 1 $dm^3_{STP}$ $min^{-1}$) of air at 773 K for 3 h (2 K $min^{-1}$).

Deposition Precipitation (DP)

To obtain 9.0 wt. % $In_2O_3$ and 1 wt. % Pd, $In(NO_3)_3 \cdot xH_2O$ (0.63 g) and $Pd(NO_3)_2 \cdot xH_2O$ (0.05 g) were dissolved in 70 $cm^3$ deionized water in a round bottom flask. $ZrO_2$ (1.80 g) was sieved to have a particle size of ≤125 μm and was added to the metal salts solution. To this mixture, an aqueous $Na_2CO_3$ solution (ca. 10 $cm^3$, 10 wt. %) was added dropwise until a pH of 9.2 was reached at which the slurry was aged for 60 min. The solid was then separated by high-pressure filtration and washed with deionized water (3 times, 500 $cm^3$ each time). Thereafter, it was then dried in a vacuum oven (1.5 kPa, 323 K, 90 min) and calcined either at 773 K for 3 h (2 K $min^{-1}$) in static air.

Co-Precipitation (CP)—Comparative Example

An example of a catalyst containing 0.75 wt. % Pd is as follows: $In(NO_3)_3 \cdot xH_2O$ (3.48 g) and $Pd(NO_3)_2 \cdot xH_2O$ (34.8 mg) were dissolved in deionized water (50 $cm^3$) in a round-bottomed flask. In a second vessel, a $Na_2CO_3$ solution was prepared by hydrolyzing $Na_2CO_3$ (10.0 g) in deionized water (100 $cm^3$). 38.8 $cm^3$ of the $Na_2CO_3$ solution were added dropwise (3 $cm^3$ $min^{-1}$) to the solution of metal nitrates under magnetic stirring at ambient temperature to reach a pH value of 9.2. The resulting slurry was aged for 60 min. After adding deionized water (50 $cm^3$), the precipitate was separated by high-pressure filtration, washed with deionized water (3 times, 500 $cm^3$ each time), dried in a vacuum oven (1.5 kPa, 323 K, 1.5 h), and calcined in static air (573 K, 3 h, 2 K $min^{-1}$).

Wet Impregnation (WI)—Comparative Example

To obtain 10 wt. % $In_2O_3$ on $ZrO_2$, $In(NO_3)_3 \cdot xH_2O$ (0.821 g) were placed in a 250 $cm^3$ round-bottom flask and dissolved in deionized water (100 cm$^3$). Then ZrO$_2$ (3.00 g, Alfa Aesar, 99.9% metals basis excluding Hf) was added and the slurry was stirred at room temperature for 30 min. The water was then removed using a rotary evaporator (100 rpm, 313 K, 8 kPa, ca. 90 min) and the sample was further dried in a vacuum oven (1.5 kPa, 323 K, ca. 90 min). Thereafter the sample was calcined at 573 K (2 K min$^{-1}$) for 3 h static air.

Example 4: Catalyst Testing

The different catalytic system including Pd/In$_2$O$_3$/ZrO$_2$ of various Pd loadings were evaluated in a methanol synthesis reaction exemplified in WO2020049081 and in WO2020049082. The results are given in Table 2.

From this table, it can be seen that the presence of palladium improves the STY by comparison to the system without palladium when applied using the correct synthesis method.

TABLE 2

Catalyst testing, all samples were measured at 280° C., 5.0 MPa, molar ratio H$_2$:CO$_2$ = 4/1, WHSV 24,000 cm$^3{}_{STP}$ g$_{cat}{}^{-1}$ h$^{-1}$

| Catalyst | Synthesis method | T$_{calcination}$ [K] | Temperature [K] | Pd$_{nominal}$ [wt. %] | In$_2$O$_3$, $_{nominal}$ [wt. %] | X$_{CO2}$ [%] | S$_{MeOH}$ [%] | STY$_{MeOH}$ [g$_{MeOH}$g$_{cat}{}^{-1}$ h$^{-1}$] |
|---|---|---|---|---|---|---|---|---|
| Ga$_2$O$_3$-Pd/SiO$_2{}^a$ | IW | 673 | 523 | 2.0 | 2.6$^b$ | 13.0 | 70.0 | 0.253 |
| 10 In$_2$O$_3$/ZrO$_2$ | WI | 573 | 553 | 0.0 | 10.00 | 4.8 | 79.0 | 0.26 |
| Pd-In$_2$O$_3$ | CP | 573 | 553 | 0.75 | 99.25 | 11.5 | 78.0 | 0.66 |
| 9.5/0.5 In$_2$O$_3$-Pd/ZrO$_2$ | WI | 573 | 553 | 0.5 | 9.50 | 6.9 | 78.8 | 0.37 |
| 9.9/0.1 In$_2$O$_3$-Pd/ZrO$_2$ | CP | 573 | 553 | 0.1 | 9.90 | 0.0 | — | 0.00 |
| 9.5/0.5 In$_2$O$_3$-Pd/ZrO$_2$ | SG | 573 | 553 | 0.5 | 9.50 | 1.3 | 98.6 | 0.09 |
| 9.9/0.1 In$_2$O$_3$-Pd/ZrO$_2$ | DP | 573 | 553 | 0.1 | 9.90 | 5.2 | 75.6 | 0.27 |
| 9.9/0.1 In$_2$O$_3$-Pd/ZrO$_2$ | DP | 773 | 553 | 0.1 | 9.90 | 6.1 | 77.8 | 0.33 |
| 9.0/1.0 In$_2$O$_3$-Pd/ZrO$_2$ | DP | 553 | 553 | 1.0 | 9.00 | 12.1 | 75.9 | 0.63 |
| 9.0/1.0 In$_2$O$_3$-Pd/ZrO$_2$ | DP | 773 | 553 | 1.0 | 9.00 | 14.0 | 73.2 | 0.70 |
| 9.0/1.0 In$_2$O$_3$-Pd/ZrO$_2$ | WI | 773 | 553 | 1.0 | 9.00 | 11.2 | 81.3 | 0.63 |

$^a$Conditions: molar ratio H$_2$:CO$_2$ = 3/1, 3.0 MPa, space velocity = 7800 h$^{-1}$. IW = incipient wetness, Reference: S. E. Collins, et al. Catal. Lett. 2005, 103, 83-88.
$^b$Ga$_2$O$_3$.

Figure 5:
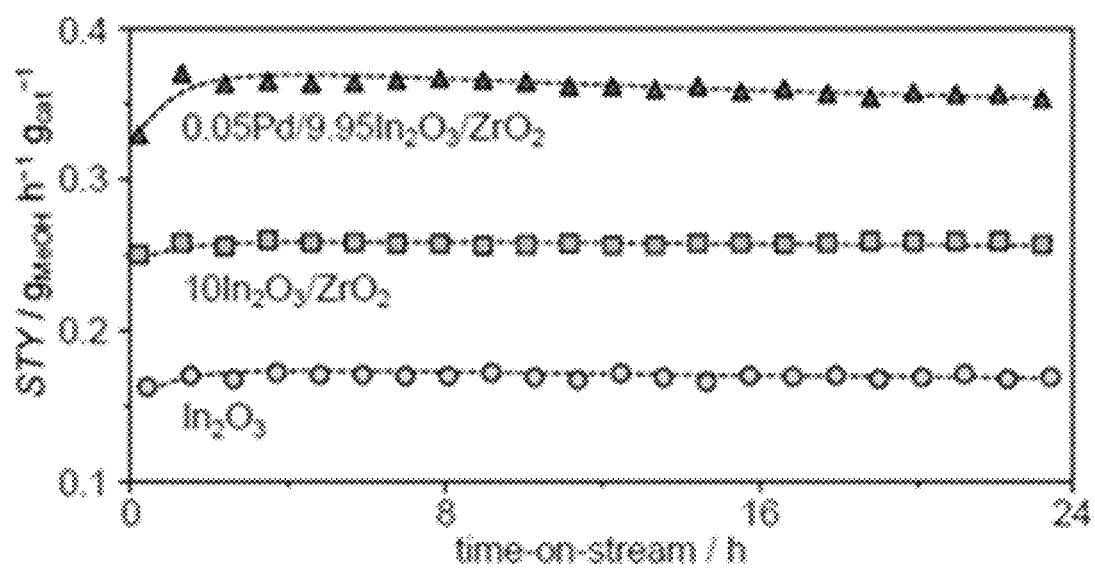
FIG. 5 demonstrates the highly stable performance of the supported catalyst $Pd/In_2O_3$ on $ZrO_2$ according to this disclosure for 24 hours, of the supported catalyst $In_2O_3$ on $ZrO_2$ and with the bulk catalyst $In_2O_3$.

Example 5: Stability of the First Catalytic Composition 9 that Comprises a First Methanol Synthesis Catalyst being an Indium Oxide Catalyst Comprising a Promoter Comprising Metal FIG. 5 reports the catalytic data collected during a 24-h test to evaluate the stability of the Pd/In$_2$O$_3$/ZrO$_2$ catalytic system (0.05 wt. % Pd loading) of the present disclosure and to compare it with the stability of the corresponding catalytic system devoid of palladium (In$_2$O$_3$/ZrO$_2$) and unsupported (In$_2$O$_3$).

Reaction conditions: 553 K (279.85° C.), 5.0 MPa, 24,000 cm$^3{}_{STP}$ g$_{cat}{}^{-1}$ h$^{-1}$, 0.1 g of catalyst, molar ratio H$_2$:CO$_2$=4:1.

After an initial STY above 0.30 g$_{MeOH}$ g$_{cat}{}^{-1}$ h$^{-1}$, a quick rise in the productivity (STY) to reach a STY of 0.36 g$_{MeOH}$ g$_{cat}{}^{-1}$ h$^{-1}$ has been observed in the first hour of the reaction. Thereafter, the productivity of the catalyst stays unaltered. By comparison with the supported catalyst devoid of palladium, the productivity (STY) was around 1.5-times higher when palladium is present. The STY of the bulk oxide (In$_2$O$_3$) is on the other hand around 2.5-times lower when compared to the STY of the ternary catalytic system of the present disclosure.

Example 6: Preparation of the Copper Zinc Oxide Catalyst

An aqueous solution of copper (II) nitrate, zinc nitrate and aluminium nitrate is prepared by adding 20 L of deionized water to a mixture comprising 2.430 kg of Cu(NO$_3$)$_3$·3H$_2$O, 1.462 kg of Zn(NO$_3$)$_2$·6H$_2$O and 5.887 kg of Al(NO$_3$)$_3$·9H$_2$O. The solution is held at a temperature of 50° C. A 20 wt. % aqueous soda solution is separately prepared and also brought to a temperature of 50° C. The two solutions are now fed separately to a stirred precipitation vessel, in which 5 L of deionized water is heated at 50° C. Both solutions are supplied by means of a pH control so as to ensure that a pH of 6.5 is maintained. After the precipitation is complete, the suspension is aged for a further hour at 50° C. while stirring, with the addition of further small amounts of metal salt solution containing copper nitrate, zinc nitrate and aluminum nitrate to keep the pH constant at 6.5.

After aging, the precipitate is filtered by a method known per se and washed with water until no more nitrate ions can be detected in the wash water. The washed filter cake is then dried at 120° C. for 16 hours. The X-ray analysis of the dried product shows, as the only crystalline phase, mixed crystals of the hydrotalcite-type of the general formula Cu$_x$Zn$_6$·Al$_2$(OH)$_{16}$CO$_3$·4H$_2$O.

The dried filter cake is then calcined for 4 hours at 350° C. in an air stream, then cooled to room temperature and then crushed to less than 1 mm, with 3% by weight of graphite powder added and compressed into tablets with a diameter of 5 mm and a height of 5 mm.

The analysis of the calcined product shows, based on the anhydrous conditions, a composition of 40 wt. % of copper oxide (CuO), 20 wt. % of zinc oxide (ZnO) and 40 wt. % of aluminum oxide (Al$_2$O$_3$).

Example 7: Stability Studies

This example illustrates the finding that the methanol catalyst in the reactor, i.e. the first methanol synthesis catalyst, can be stable in presence of a $CO_2$-rich feedstream provided that the temperature conditions are high. The use of the said catalyst in the first reactor at high temperature allows the $CO_2/CO$ molar ratio of the feedstream to be reduced at the entry of the one or more second reactor, so the second reactor can be operated at a lower temperature with catalyst stability.

The first methanol synthesis catalyst is Cu—ZnO—$Al_2O_3/ZrO_2$.

The first reaction conditions have been carried out 225° C. (low-temperature LT) or at 275° C. (high-temperature HT) and at a pressure of 5.0 MPa, with a syngas having a molar ratio of hydrogen to carbon dioxide of 3, and with a GHSV of the syngas feedstream of 2600 $h^{-1}$.

The second methanol synthesis catalyst is Cu—ZnO—$Al_2O_3/ZrO_2$.

The second reaction conditions have been carried out 225° C. and at a pressure of 5.0 MPa, with a GHSV of the first gaseous effluent of 2600 $h^{-1}$.

Figure 6:
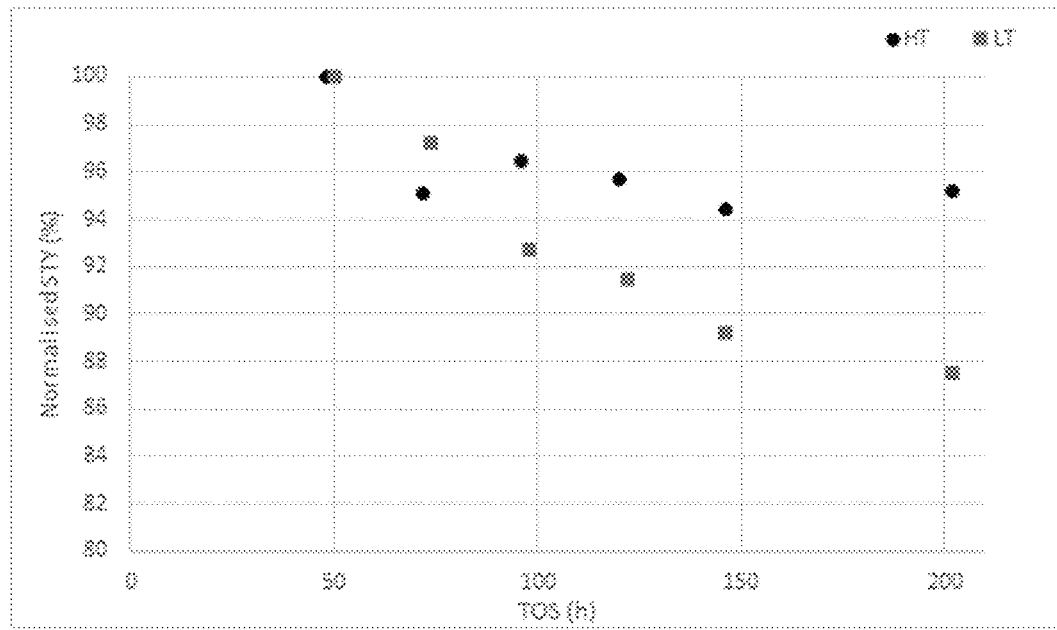
FIG. 6 shows the normalized space time yield in methanol in function of the time on stream (TOS) of the second methanol synthesis catalyst, being $Cu\text{—}ZnO\text{—}Al_2O_3/ZrO_2$.

FIG. 6 shows the normalized yield in methanol in function of the time on stream (TOS) of the second methanol synthesis catalyst. The TOS is amounting to 202 hours. It is thus demonstrated that the second methanol catalyst is more stable when the first temperature conditions in the first reactor 11 were of 275° C. (HT) than of 225° C. (LT). The yield is always above 94% when the first reactor 11 has been worked at 275° C. while it drops below 94% when the first temperature conditions are of 225° C.

Figure 7:
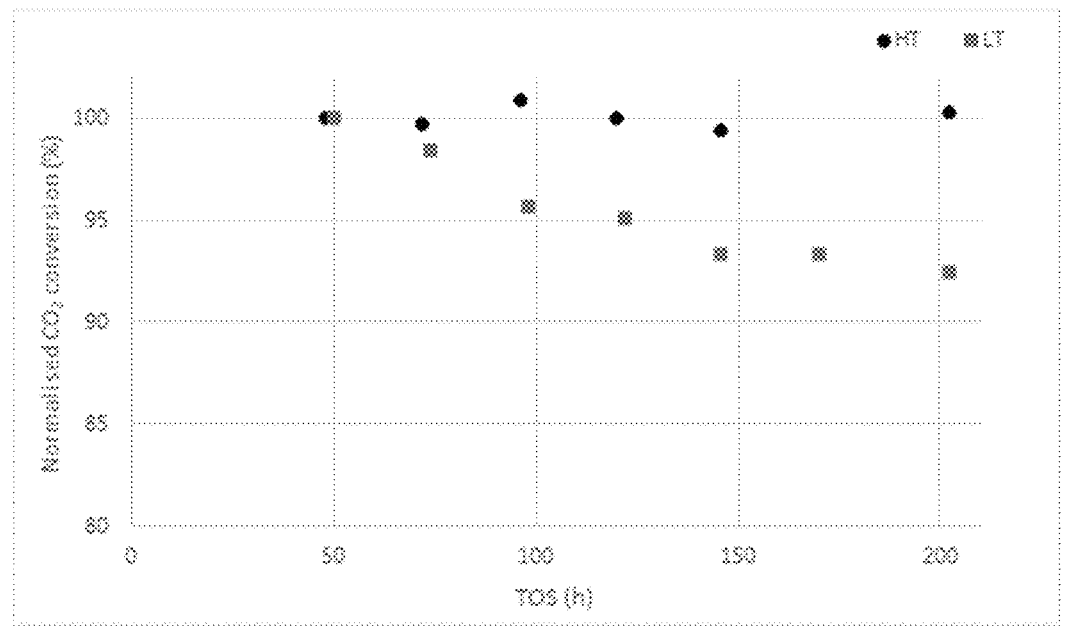
FIG. 7 shows the normalized conversion of carbon dioxide in function of the time on stream (TOS) of the second methanol synthesis catalyst, being $Cu\text{—}ZnO\text{—}Al_2O_3/ZrO_2$.

FIG. 7 shows the normalized conversion of carbon dioxide in function of the time on stream (TOS) of the second methanol synthesis catalyst. The TOS is amounting to 202 hours. It is thus demonstrated that the second methanol catalyst is more stable when the first temperature conditions in the first reactor 11 were of 275° C. (HT) than of 225° C. (LT). The conversion is also always above 95% while when the first reactor has been worked at a lower temperature, the conversion drops below 95% after about 100 hours.

Figure 8:
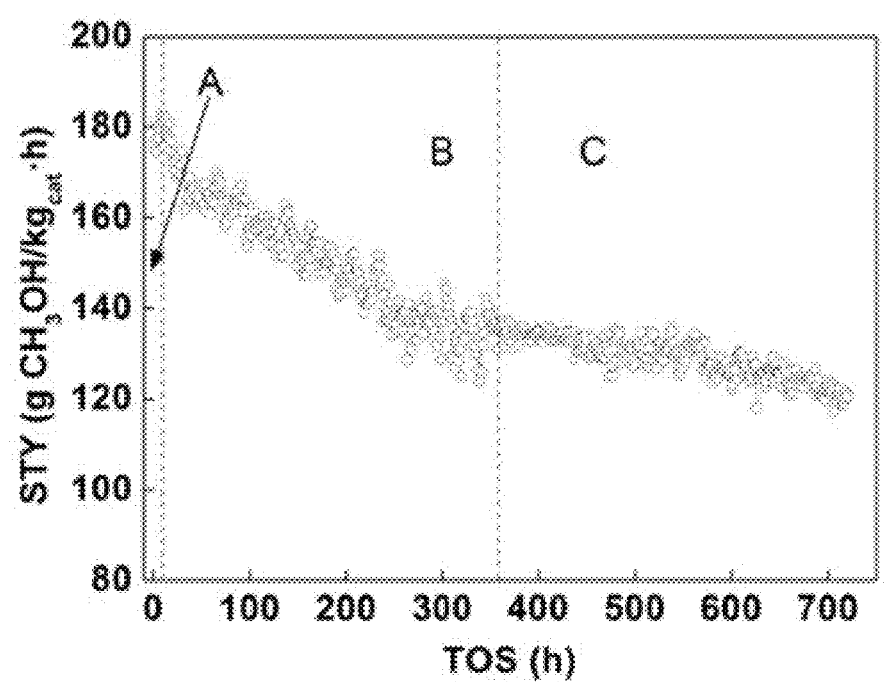
FIG. 8 shows STY of $CH_3OH$ over a $CuZnOAl_2O_3$ catalyst with the TOS of 720 h in $CO_2$ hydrogenation. Reaction conditions: $H_2/CO_2=3:1$; temperature=200° C.; pressure=30 bar; GHSV=9000 $h^{-1}$.

FIG. 8 illustrates the deactivation of a Cu-based catalyst in $CO_2$ pure streams at mild temperatures as shown by Huang et al. (Ind. Eng. Chem. Res., 2019, 58, 9030-9037) in which the deactivation of $Cu/ZnO/Al_2O_3$ for $CO_2$ to methanol was studied.

Example 8: Methanol Synthesis Simulation

All the following cases result from simulations carried out on ASPEN PLUS V9 software.

The first methanol synthesis catalyst is Cu—ZnO—$Al_2O_3/ZrO_2$.

The first reaction conditions have been simulated at 225° C., 275° C. or 340° C. and at a pressure of 7.0 MPa, with a syngas having a molar ratio of hydrogen to carbon dioxide of 3, and with a GHSV of the syngas feedstream of 2600 $h^{-1}$.

The second methanol synthesis catalyst is Cu—ZnO—$Al_2O_3/ZrO_2$.

The second reaction conditions have been carried out 225° C. and at a pressure of 7.0 MPa, with a GHSV of the first gaseous effluent of 2600 $h^{-1}$.

For all cases, the feed rate at the inlet of the system is 100 kmol/h. The $H_2/(CO_2+CO)$ molar ratio is 3; with CO=0. The yield expresses the mol content of MeOH produced per 100 mol of $CO_2$ fed.

Cases 1 and 2: Methanol Synthesis in One or Two Reactors

TABLE 3

Case 1 (one reactor) is shown in the 3 first rows and case 2 (two reactors) is shown in the 2 following rows. In the below table the $CO_2/CO$ molar ratio at the entry of the system was infinite (i.e. pure $CO_2$), the $CO_2/CO$ molar ratio in the third column is the $CO_2/CO$ molar ratio at the entry of the single reactor for case 1 and at the input of the second reactor for case 2. The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C.) | CO (mol %) | $CO_2/CO$ | $CO_2$ (mol %) | x $CO_2$ (%) | $Yield_{MeOH}$ (mol %) |
|---|---|---|---|---|---|
| 225 | — | ∞ | 25 | 38.4 | 34.7 |
| 275 | — | ∞ | 25 | 29.6 | 18.5 |
| 340 | — | ∞ | 25 | 31.0 | 5.1 |
| 275 | 2.44 | 8.00 | 19.5 | 38.4 | 34.7 |
| 340 | 6.47 | 2.75 | 17.79 | 38.4 | 34.7 | n.a.: non-applicable

Comparison Between Case 1 and Case 2

The incorporation of a second reactor comprising a second methanol synthesis catalyst downstream of a first reactor comprising a first methanol synthesis catalyst allows having a decreasing $CO_2/CO$ molar ratio at the input of the second reactor 19 (from 8.0 mol/mol to 2.7 mol/mol). This effect is observed only when the temperature is increased to at least 270° C., in particular at 275° C. or more such as 340° C.

Case 3: Introduction of Intermediate Gas/Liquid Separator Between the Two Reactors

TABLE 4

Case 3 - two reactors with an intermediate gas/liquid separator in between The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C) | CO (mol %) | $CO_2/CO$ | $CO_2$ (mol %) | x $CO_2$ (%) | $Yield_{MeOH}$ (mol %) |
|---|---|---|---|---|---|
| 225 | 0.96 | 24.6 | 23.6 | 62.1 | 23.5 |
| 275 | 3.13 | 7.14 | 22.3 | 53.9 | 31.5 |
| 340 | 7.13 | 2.74 | 19.5 | 51.0 | 41.4 | n.a.: non-applicable

The incorporation of intermediate gas/liquid separator between the first reactor and the second reactor to separate from the first gaseous effluent a $CO_2$-enriched gaseous stream and a CO-enriched gaseous stream allows, when the temperature of the first reactor is elevated (i.e., 340° C.) to obtain a yield of methanol superior of 40 mol %. This is so far the best results in comparison with the base case (only one reactor, i.e. case 1) and with case 2 where there is only a direct line without intermediate gas/liquid separator between the first and the second reactor.

Case 4: Introduction of a Recycle Step

TABLE 5

Case 4 - one reactor with a recycle step, according to which the gaseous effluent exiting the reactor is recycled to be put into contact again with the catalytic composition present in the reactor. The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C) | CO (mol %) | $CO_2/CO$ | $CO_2$ (mol %) | x $CO_2$ (%) | $Yield_{MeOH}$ (mol %) | Recycle (kmol/h) | |
|---|---|---|---|---|---|---|---|
| 225 | 0.44 | 18.9 | 8.31 | 96.5 | 96.3 | 184 | n.a. |
| 275 | 0.52 | 18.0 | 9.36 | 94.7 | 93.9 | 328 | n.a. |
| 340 | 0.90 | 11.3 | 10.2 | 92.6 | 86.4 | 735 | n.a. | n.a.: non-applicable

The incorporation of a recycling step which has the purpose of redirecting the gaseous effluent exiting the reactor into said reactor has allowed to considerably increase both the conversion in $CO_2$ and the yield in methanol. Indeed, the conversion of $CO_2$ is above 90% at all studied temperature and the yield in methanol is at least 85%, while in the base case, namely without recycle step, the conversion of $CO_2$ is lower than 40% and the yield in methanol is lower than 35%. The $CO_2/CO$ molar ratio at the exit of the reactor is always above 10. Since this result is a major improvement, it was decided to incorporate a recycling step to case 2, namely to the case where two reactors were disposed (cf. case 5 below).

Case 5: Two Reactors with a Recycle Step from the Second to the First Reactor

TABLE 6

Case 5 - two reactors with a recycle step, according to which the second gaseous effluent exiting the second reactor is recycled to be put into contact again with the first catalytic composition present in the first reactor.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C) | CO (mol %) | $CO_2/CO$ | $CO_2$ (mol %) | x $CO_2$ (%) | $Yield_{MeOH}$ (mol %) | Recycle (kmol/h) R2 to R1 | |
|---|---|---|---|---|---|---|---|
| 275 | 2.14 | 5.45 | 11.7 | 96.5 | 96.3 | 184 | n.a. |
| 340 | 5.46 | 1.98 | 10.8 | 96.5 | 96.3 | 184 | n.a. | n.a.: non-applicable

Case 5 has been conducted with elevated temperature (i.e. 275° C. and 340° C.) for the first reactor. This has allowed keeping the recycle rate low (184 kmol/hour). The $CO_2/CO$ molar ratio at the input of the second reactor has also decreased (i.e., below 6), which was not possible when doing the conversion of syngas to methanol with only one reactor and the recycling step (in comparison with case 4), where such molar ratio was superior to 10. The introduction of the recycle step according to which the second gaseous effluent exiting the second reactor is recycled and thus redirected to the first reactor, has allowed obtaining results of at least 96% in term of both the conversion of $CO_2$ and the yield of methanol.

Case 6: Two Reactors with a Recycle Step from the Second to the First Reactor and a Separation in Between

TABLE 7

Case 6 - two reactors with a recycle step, according to which the second gaseous effluent 23 exiting the second reactor 19 is recycled to be put into contact again with the first catalytic composition 9 present in the first reactor 11, and with an intermediate gas/liquid separator 47 in between the two reactors.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C.) | CO (mol %) | $CO_2/CO$ | $CO_2$ (mol %) | x $CO_2$ (%) | $Yield_{MeOH}$ (mol %) | Recycle (kmol/h) R2 to R1 | |
|---|---|---|---|---|---|---|---|
| 225 | 0.63 | 18.2 | 11.4 | 98.0 | 98.0 | 86 | n.a. |
| 275 | 2.35 | 5.34 | 12.5 | 97.7 | 97.6 | 110 | n.a. |
| 340 | 5.87 | 1.91 | 11.2 | 97.4 | 97.3 | 126 | n.a. | n.a.: non-applicable

Interesting to note that by conducting the process with a temperature within the first reactor 11 of 340° C., it was possible to obtain a $CO_2/CO$ molar ratio inferior to 2 at the input of the second reactor 19.

When introducing an intermediate gas/liquid separator 47 between the first reactor 11 and the second reactor 19 to separate from the first gaseous effluent 15 a fourth liquid effluent 39 comprising methanol and water and a fourth gaseous effluent 41, while at the same time performing a recycled step in which the second gaseous effluent 23 is redirected towards the first catalytic composition 9, not only the recycle rate has decreased (below 140 at all temperatures), but both the conversion of $CO_2$ and the yield in methanol have (slightly) increased when compared with case 5. Indeed, both the conversion of $CO_2$ and the yield in methanol in case 6 are above 97%.

In the following two cases (cases 7a and 7b), a recycle on the first reactor has been studied with a different split of the recycle, respectively 80/20 and 90/10. In case of 7a, 80% of the first gaseous effluent 15 exiting the first reactor 11 is recycled to be put into contact again with the first catalytic composition 9 present in the first reactor 11, while in case of 7b, this is 90% of the first gaseous effluent 15 which is recycled.

Case 7a: Two Reactors with a First-Reactor-Recycle Step Carried Out at Split 80/20, Namely a Recycle Step on the First Reactor, and an Intermediate Gas/Liquid Separator in Between the Two Reactors

TABLE 8

Case 7a - two reactors with a recycle step, according to which 80% of the first gaseous effluent 15 exiting the first reactor 11 is recycled to be put into contact again with the first catalytic composition 9 present in the first reactor 11, implemented with an intermediate gas/liquid separator 47 and a splitter 49 in between the two reactors.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C.) | CO (mol %) | $CO_2/CO$ | $CO_2$ (mol %) | x $CO_2$ (%) | $Yield_{MeOH}$ (mol %) | Recycle (kmol/h) R1 to R1 | |
|---|---|---|---|---|---|---|---|
| 225 | 0.96 | 23.2 | 22.2 | 83.2 | 82.2 | 103 | n.a. |
| 275 | 3.58 | 5.94 | 21.3 | 75.2 | 73.4 | 162 | n.a. |
| 340 | 11.0 | 1.50 | 16.5 | 67.6 | 64.0 | 252 | n.a. | n.a.: non-applicable

Case 7b: Two Reactors with a First-Reactor-Recycle Step Carried Out at Split 90/10, Namely a Recycle Step on the First Reactor, and an Intermediate Gas/Liquid Separator in Between the Two Reactors

TABLE 9

Case 7b - two reactors with a recycle step, according to which 90% of the first gaseous effluent 15 exiting the first reactor 11 is recycled to be put into contact again with the first catalytic composition 9 present in the first reactor 11, implemented with an intermediate gas/liquid separator 47 and a splitter 49 in between the two reactors.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C) | CO (mol %) | $CO_2/CO$ | $CO_2$ (mol %) | x $CO_2$ (%) | $Yield_{MeOH}$ (mol %) | Recycle (kmol/h) R1 to R1 | |
|---|---|---|---|---|---|---|---|
| 225 | 0.92 | 22.5 | 20.7 | 89.8 | 89.3 | 133 | n.a. |
| 275 | 3.57 | 5.70 | 20.3 | 84.1 | 82.9 | 228 | n.a. |
| 340 | 12.1 | 1.26 | 15.2 | 76.9 | 74.1 | 413 | n.a. |

Cases 7a and 7b demonstrate that more the amount of recycle on the first reactor is elevated, better is both the conversion of $CO_2$ and the yield in methanol.

Case 8: Two Reactors with a Second-Reactor-Recycle Step, Namely a Recycle Step on the Second Reactor and an Intermediate Gas/Liquid Separator in Between the Two Reactors

TABLE 10

Case 8 - two reactors with a recycle step, according to which the second gaseous effluent 23 exiting the second reactor 19 is recycled to be put into contact again with the second catalytic composition 17 present in the second reactor 19 implemented by a final gas/liquid separator 27 and a splitter 33 disposed downstream of said second reactor 19, and with an intermediate gas/liquid separator 47 in between the two reactors.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C) | CO (mol %) | $CO_2/CO$ | $CO_2$ (mol %) | x $CO_2$ (%) | $Yield_{MeOH}$ (mol %) | Recycle (kmol/h) R2 to R2 | |
|---|---|---|---|---|---|---|---|
| 225 | 0.65 | 19.2 | 12.5 | 97.1 | 97.0 | 138 | n.a. |
| 275 | 1.49 | 9.53 | 14.2 | 97.0 | 96.9 | 150 | n.a. |
| 340 | 3.03 | 4.60 | 13.9 | 96.9 | 96.8 | 157 | n.a. | n.a.: non-applicable

It is demonstrated that the $CO_2/CO$ molar ratio at the input of the second reactor 19 is slightly higher when the recycle step is done on the second reactor only and not from the second to the first reactor as in case 6. Even if the conversion and yield are interesting, the $CO_2/CO$ molar ratio at the input of the second reactor is not entirely satisfactory.

When applying a second-reactor-recycle step, namely a recycle step on the second reactor only, and not from the second to the first reactor as in case 6, it has been demonstrated that, although both the conversion of $CO_2$ and the yield in methanol are above 96%, it is more efficient to set up the configuration as in case 6 than in the present case 8, as both the conversion of $CO_2$ and the yield in methanol in case 6 are above 97%.

Finally, in the following two cases (cases 9a and 9b), a configuration with a first-reactor-recycle step and a second-reactor-recycle step, namely with both a recycle on the first reactor and the second reactor has been studied (see FIG. 2). The recycle on the first reactor (i.e. the first-reactor-recycle step) has been studied with a different split of the recycle, respectively 80/20 and 90/10. In case of 9a, 80% of the first gaseous effluent 15 exiting the first reactor 11 is recycled to be put into contact again with the first catalytic composition 9 present in the first reactor 11, while in case of 9b, this is 90% of the first gaseous effluent 15 which is recycled.

Case 9a: Two Reactors with a First-Reactor-Recycle Step Carried Out at Split 80/20, a Second-Reactor-Recycle Step

TABLE 11

Case 9a - two reactors with a first-reactor-recycle step, according to which 80% of the first gaseous effluent 15 exiting the first reactor 11 is recycled to be put into contact again with the first catalytic composition 9 present in the first reactor 11, implemented by an intermediate gas/liquid separator 47 and a splitter 49 in between the two reactors, and with a second-reactor-recycle step, implemented by a final gas/liquid separator 27 and a splitter 33 disposed downstream of said second reactor 19.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C.) | CO (mol %) | $CO_2/CO$ | $CO_2$ (mol %) | x $CO_2$ (%) | $Yield_{MeOH}$ (mol %) | Recycle (kmol/h) R1 to R1 | R2 to R2 |
|---|---|---|---|---|---|---|---|
| 225 | 0.34 | 15.5 | 5.3 | 97.0 | 96.7 | 103 | 111 |
| 275 | 1.03 | 6.51 | 6.70 | 97.5 | 97.2 | 162 | 136 |
| 340 | 3.51 | 2.17 | 7.62 | 98.3 | 97.0 | 251 | 151 |

Case 9b: Two Reactors with a First-Reactor-Recycle Step Carried Out at Split 90/10, a Second-Reactor-Recycle Step

TABLE 12

Case 9b - two reactors with a first-reactor-recycle step, according to which 90% of the first gaseous effluent 15 exiting the first reactor 11 is recycled to be put into contact again with the first catalytic composition 9 present in the first reactor 11, implemented by an intermediate gas/liquid separator 47 and a splitter 49 in between the two reactors, and with a second-reactor-recycle step, implemented by a final gas/liquid separator 27 and a splitter 33 disposed downstream of said second reactor 19. The recycle is given in kmole/hour.
The CO (mol %), the $CO_2$ (mol %) and $CO_2/CO$ ratio are determined at the inlet of the second reactor. The $xCO_2$ (%) and the $Yield_{MeOH}$ (mol %) are given for the overall system.

| T1 (° C.) | CO (mol %) | $CO_2/CO$ | $CO_2$ (mol %) | x $CO_2$ (%) | $Yield_{MeOH}$ (mol %) | Recycle (kmol/h) R1 to R1 | R2 to R2 |
|---|---|---|---|---|---|---|---|
| 225 | 0.16 | 13.6 | 2.18 | 96.9 | 96.8 | 133 | 138 |
| 275 | 0.76 | 5.72 | 4.35 | 97.3 | 97.1 | 228 | 123 |
| 340 | 4.26 | 1.99 | 8.48 | 98.0 | 97.7 | 413 | 97 |

From the comparison between case 9a and case 9b, it is clear that more the amount of recycle on the first reactor is elevated, better is both the conversion of $CO_2$ and the yield in methanol, as this was already demonstrated with case 7a and case 7b.

Although both the conversion of $CO_2$ and the yield in methanol are elevated when a first-reactor-recycle step, a second-reactor-recycle step and a splitter in between the two reactors the $CO_2/CO$ molar ratio is similar (slightly higher) than in case 6, namely in a configuration in which the recycle is performed from the second reactor to the first reactor (and with no recycle on individual reactor) but the recycle rate is increased by comparison to case 6 and the $CO_2$ conversion is decreased.

Indeed, with a temperature in the first reactor of 340° C., the $CO_2/CO$ molar ratio in case 9b is 2.0 while in case 6 is 1.9. With a temperature in the first reactor of 275° C., the $CO_2/CO$ molar ratio in case 9b is 5.7 while in case 6 is 5.3. This means that the incorporation of a recycling step from the second reactor to the first reactor, as in case 6, allows enhancing the stability of the second catalytic composition 19 which is present in the second reactor 19. The lower $CO_2/CO$ molar ratio at the input of the second reactor 19, namely in the first gaseous effluent 15 allows therefore not to deactivate or to deactivate to a lesser degree the second catalytic composition.

This fact was experimentally demonstrated in example 2.

The invention claimed is:

1. A process for methanol synthesis characterized in that it comprises the following steps:
   a) providing a syngas feedstreamcomprising hydrogen and carbon oxides, wherein the carbon oxides are selected from carbon dioxide or a mixture of carbon dioxide and carbon monoxide provided that the molar ratio of carbon dioxide over carbon monoxide in the mixture is equal to or greater than 1.0, and that said syngas feedstream comprises at least 12.0 mol % of $CO_2$ based on the total molar content of said syngas feedstream;
   b) providing a first catalytic composition that comprises at least one first methanol synthesis catalyst;
   c) putting into contact said syngas feedstream with said first catalytic composition under first reaction conditions comprising first temperature conditions, to provide a first gaseous effluent and optionally a first liquid effluent;
   d) providing a second catalytic composition that comprises at least one second methanol synthesis catalyst wherein said at least one second methanol synthesis catalyst is the same or different from said one first methanol synthesis catalyst;
   e) putting into contact at least a part of said first gaseous effluent with the second catalytic composition under second reaction conditions comprising second temperature conditions, to provide a second gaseous effluent and a second liquid effluent;
   f) recovering methanol from one or more selected from the first gaseous effluent and the second gaseous effluent;
wherein the first temperature conditions are at least 275° C., wherein the second temperature conditions are lower than the first temperature conditions and second temperature conditions are ranging between 180° C. and 250° C.,
wherein said first gaseous effluent is subjected to a separation step before being put into contact with the second catalytic composition in step (e) to remove at least a part of methanol and water;
   wherein at least a part of the second gaseous effluent is recycled to be put into contact with said first catalytic composition again.

2. The process according to claim 1, characterized in that said syngas feedstream comprises more than at least 15.0 mol % to more than at least 20.0 mol % of $CO_2$ based on the total molar content of said syngas feedstream.

3. The process according to claim 1, characterized in that the carbon oxides present in the syngas feedstream is a mixture of carbon dioxide and carbon monoxide, said mixture has a molar ratio of carbon dioxide over carbon monoxide equal to or greater than 2.0.

4. The process according to claim 1, characterized in that the carbon oxides present in the syngas feedstream is a mixture of carbon dioxide and carbon monoxide, said mixture has a molar ratio of carbon dioxide over carbon monoxide equal to or greater than 3.0.

5. The process according to claim 1, characterized in that the molar ratio of hydrogen to carbon dioxide in the syngas feedstream is at least 2.0.

6. The process according to claim 1, characterized in that the first gaseous effluent comprises at least 1.0 mol % of methanol based on the total molar content of the first gaseous effluent.

7. The process according to claim 1, characterized in that the first temperature conditions comprise a temperature ranging between 275° C. and 350° C.

8. The process according to claim 1, characterized in that the first temperature conditions the first temperature conditions are at least 280° C.

9. The process according to claim 1, characterized in that the first temperature conditions the first temperature conditions are at least 290° C.

10. The process according to claim 1, characterized in that the first temperature conditions the first temperature conditions are at least 300° C.

11. The process according to claim 1, characterized in that the at least one first methanol synthesis catalyst and the at least one second methanol synthesis catalyst are the same.

12. The process according to claim 1, characterized in that the at least one first methanol synthesis catalyst and/or the at least one second methanol synthesis catalyst is or comprises a copper zinc oxide catalyst; wherein, the copper zinc oxide catalyst is prepared by co-precipitation.

13. The process according to claim 1, characterized in that the at least one first methanol synthesis catalyst and/or the at least one second methanol synthesis catalyst is or comprises an indium oxide catalyst; wherein, said indium oxide catalyst comprises a promoter comprising at least one metal.

14. The process according to claim 13, characterized in that when an indium oxide catalyst comprises a promoter comprising at least one metal, said at least one metal is selected from ruthenium, rhodium, gold, iridium, palladium, silver, osmium, platinum, copper, nickel, cobalt and any combinations thereof.

15. The process according to claim 1, characterized in that the at least one first methanol synthesis catalyst and/or the at least one second methanol synthesis catalyst is or comprises one or more selected from an indium oxide catalyst, Cu—ZnO, Cu—ZnO/$Al_2O_3$, Cu—ZnO—$Ga_2O_3$/$SiO_2$, Cu—ZnO—$Al_2O_3$/$ZrO_2$, ZnO, Au/ZnO, Au/$Fe_2O_3$, Au/$TiO_2$, Au/$ZrO_2$, Au/$La_2O_3$, Au/$ZnFe_2O_4$, $Fe_2O_3$, Au/$Fe_2O_3$, $CeO_2$, $TiO_2$, $ZrO_2$, $La_2O_3$, Zn/$Fe_2O_3$.

16. The process according to claim 1, characterized in that at least a part of the second gaseous effluent is recycled to be put into contact with said first catalytic composition again.

17. A method of using at least one first catalytic composition that comprises at least one first methanol synthesis catalyst in the process for methanol synthesis according to claim 1, wherein said method is characterized in that it is performed in an installation comprising at least two reactors in series wherein
   a first reactor comprises said at least one first catalytic composition, and
   at least one subsequent reactor placed downstream of said first reactor comprises at least one second catalytic composition comprising at least one second methanol synthesis catalyst wherein at least one second methanol synthesis catalyst is the same or different from one first methanol synthesis catalyst;

wherein the method comprises providing a syngas feedstream comprising hydrogen and carbon oxides to the first reactor to contact said syngas feedstream with said at least first catalytic composition, wherein the carbon oxides are selected from carbon dioxide or a mixture of carbon dioxide and carbon monoxide provided that the molar ratio of carbon dioxide over carbon monoxide in the mixture is equal to or greater than 1.0; wherein said syngas feedstream comprises at least 12.0 mol % of $CO_2$ based on the total molar content of said syngas feedstream;

wherein the temperature within said first reactor is at least 275° C. and further wherein the second temperature conditions are lower than the first temperature conditions and second temperature conditions are ranging between 180° ° C.and 250° C.; and wherein the installation further comprises a first gas/liquid separator disposed between the first reactor and at least one subsequent reactor.

18. The method of claim 17, characterized in that the at least one subsequent reactor comprising said at least one second catalytic composition forms at least one subsequent catalytic bed, and at least one reverse water-gas shift catalyst is introduced at the end of said one or more subsequent catalytic beds; wherein said one or more reverse water-gas shift catalysts are selected from $Fe_2O_3$, $ZnNiFe_2O_4$, $Ba-Fe_3O_3-Al_2O_3-NiO$, Cu-Mn spinel oxide, $La_{2-x}Ca_xCuO_4$, oxide supported Cu, $CuO/ZrO_2$, $CeO_2/CuO$, oxide supported Au, and $Cu-CeO_2-La_2O_3$.

19. A process for methanol synthesis characterized in that it comprises the following steps:
   a) providing a syngas feedstream comprising hydrogen and carbon oxides, wherein the carbon oxides are selected from carbon dioxide or a mixture of carbon dioxide and carbon monoxide provided that the molar ratio of carbon dioxide over carbon monoxide in the mixture is equal to or greater than 1.0, and that said syngas feedstream comprises at least 12.0 mol % of $CO_2$ based on the total molar content of said syngas feedstream;
   b) providing a first catalytic composition that comprises at least one first methanol synthesis catalyst;
   c) putting into contact said syngas feedstream with said first catalytic composition under first reaction conditions comprising first temperature conditions, to provide a first gaseous effluent and optionally a first liquid effluent;
   d) providing a second catalytic composition that comprises at least one second methanol synthesis catalyst wherein said at least one second methanol synthesis catalyst is the same or different from said one first methanol synthesis catalyst;
   e) putting into contact at least a part of said first gaseous effluent with the second catalytic composition under second reaction conditions comprising second temperature conditions, to provide a second gaseous effluent and a second liquid effluent;
   f) recovering methanol from one or more selected from the first gaseous effluent and the second gaseous effluent;

wherein the first temperature conditions are at least 275° C., wherein the second temperature conditions are lower than the first temperature conditions and second temperature conditions are ranging between 180° C. and 250° C., wherein said first gaseous effluent is subjected to a separation step before being put into contact with the second catalytic composition in step (e) to remove at least a part of methanol and water, and and wherein at least a part of the first gaseous effluent is recycled to be put into contact with said first catalytic composition again and at least a part of the second gaseous effluent is recycled to be put into contact with said second catalytic composition again.

20. The process according to claim 1, characterized in that the carbon oxides present in the syngas feedstream is a mixture of carbon dioxide and carbon monoxide, said mixture has a molar ratio of carbon dioxide over carbon monoxide equal to or greater than 2.5.

* * * * *